US008874230B2

United States Patent
Niver et al.

(10) Patent No.: US 8,874,230 B2
(45) Date of Patent: Oct. 28, 2014

(54) INTEGRATED FIBER OPTIC RAMAN SPECTROSCOPY AND RADIO FREQUENCY ABLATION

(75) Inventors: Edip Niver, Mountainside, NJ (US); Kenneth W. Lieberman, Tenafly, NJ (US)

(73) Assignee: New Jersey Institute of Technology, Newark, NJ (US)

( * ) Notice: Subject to any disclaimer, the term of this patent is extended or adjusted under 35 U.S.C. 154(b) by 422 days.

(21) Appl. No.: 13/121,346

(22) PCT Filed: Aug. 4, 2010

(86) PCT No.: PCT/US2010/044438
§ 371 (c)(1),
(2), (4) Date: Mar. 28, 2011

(87) PCT Pub. No.: WO2011/025640
PCT Pub. Date: Mar. 3, 2011

(65) Prior Publication Data
US 2011/0190760 A1 Aug. 4, 2011

Related U.S. Application Data

(60) Provisional application No. 61/237,338, filed on Aug. 27, 2009.

(51) Int. Cl.
*A61B 18/18* (2006.01)
*A61B 5/00* (2006.01)
*A61B 1/00* (2006.01)
*A61B 18/00* (2006.01)
*A61B 17/00* (2006.01)

(52) U.S. Cl.
CPC ........... *A61B 5/0075* (2013.01); *A61B 1/00165* (2013.01); *A61B 5/0084* (2013.01); *A61B 2018/00642* (2013.01); *A61B 2017/00084* (2013.01)
USPC ................ 607/101; 607/100; 606/33; 606/41

(58) Field of Classification Search
CPC .... A61B 5/075; A61B 5/084; A61B 1/00165; A61B 1/0167; A61B 2018/00642
USPC ............................... 607/100, 101; 606/33, 41
See application file for complete search history.

(56) References Cited

U.S. PATENT DOCUMENTS 7,383,077 B2   6/2008   Zeng
7,653,428 B2   1/2010   Goldstein et al.

(Continued)

OTHER PUBLICATIONS

Baere, T.D. et al, "Long Term Follow up after Percutaneous Pulmonary Radiofrequency Ablation," Journal of Vascular and Interventional Radiology, 2008, vol. 19, No. 2 Supplement p. S42.

(Continued)

*Primary Examiner* — Linda Dvorak
*Assistant Examiner* — Kaitlyn Smith
(74) *Attorney, Agent, or Firm* — Turk IP Law, LLC

(57) ABSTRACT

Technologies are generally described for detecting diseased tissues through fiber optic based Raman spectroscopy, image acquisition, and/or RF induced hyperthermia treatment of the detected tissues in an integrated manner. A fiber optic bundle for carrying optical and RF signals for the spectroscopy, visual imaging, and RF ablation may also be used to detect a temperature of the treated tissue such that level and duration of the RF signal can be controlled for optimum results. A shielding configuration in the form of a coaxial waveguide of the fiber optic bundle may be used to guide and deliver the RF signal. Sources and detectors for the optical and RF signals may be integrated into an endoscopic probe containing the fiber optic bundle or be externally positioned. An integrated or remote controller may be employed to manage the optical imaging, spectroscopy, RF ablation, and thermal sensing operations.

27 Claims, 11 Drawing Sheets

(56) References Cited

U.S. PATENT DOCUMENTS

| | | | |
|---|---|---|---|
| 7,656,522 | B2 | 2/2010 | Puppels et al. |
| 7,659,977 | B2 | 2/2010 | Koo |
| 7,688,440 | B2 | 3/2010 | Clarke et al. |
| 7,697,576 | B2 | 4/2010 | Maier et al. |
| 7,912,553 | B2* | 3/2011 | Nishizawa .................. 607/101 |
| 2004/0064023 | A1* | 4/2004 | Ryan et al. .................. 600/374 |
| 2005/0117150 | A1 | 6/2005 | Puppels et al. |
| 2005/0277816 | A1 | 12/2005 | Maier et al. |
| 2006/0030753 | A1* | 2/2006 | Boutillette et al. ........... 600/146 |
| 2006/0058782 | A1* | 3/2006 | Truckai et al. ................. 606/41 |
| 2006/0287649 | A1 | 12/2006 | Ormsby et al. |
| 2007/0038127 | A1 | 2/2007 | Goldstein et al. |
| 2007/0224683 | A1 | 9/2007 | Clarke et al. |
| 2007/0247620 | A1 | 10/2007 | Koo |
| 2009/0012378 | A1 | 1/2009 | Ince |
| 2009/0093728 | A1 | 4/2009 | Hyde et al. |
| 2009/0143774 | A1 | 6/2009 | Uzunbajakava et al. |
| 2010/0249601 | A1* | 9/2010 | Courtney ...................... 600/463 |
| 2011/0213206 | A1* | 9/2011 | Boutillette et al. ........... 600/146 |
| 2012/0150164 | A1* | 6/2012 | Lee et al. ......................... 606/16 |
| 2012/0316558 | A1* | 12/2012 | Hendriks et al. ................. 606/41 |
| 2014/0046129 | A1* | 2/2014 | Boutillette et al. ........... 600/104 |

OTHER PUBLICATIONS

Callstrom et al., "Percutaneous Ablation: Safe, Effective Treatment of Bone Tumors," Oncology, 2005, vol. 19, No. 11, pp. 22-26.
Hafez et al., "Radiofrequency Catheter Ablation in Children with Supraventricular Tachycardias: Intermediate Term Follow Up Results," Clinical Medicine Insights: Cardiology 2012, vol. 6, pp. 7-16.
Weiss et al., "Radiofrequency Ablation Therapy for Varicose Veins," Medscape Reference, Updated Jan. 23, 2012, pp. 1-6. Retrieved from URL:<http://emedicine.medscape.com/article/1085800-overview> on Jan. 30, 2013.
Lambert et al., "Raman spectroscopy: the gateway into tomorrow's virology," Virology Journal, 2006, 3:51.
Mahadevan-Jansen, A., "Raman Spectroscopy: From Benchtop to Bedside," Biomedical Photonics Handbook, Chapter 30, CRC Press, Boca Raton, 2003.
International Search Report and Written Opinion for International Application No. PCT/US2010/044438 mailed on Dec. 3, 2010.
Harris et al., "Raman spectroscopy in head and neck cancer," Head & Neck Oncology, 2010, 2:26.
Rosen, A, and Rosen, H., "The efficacy of transurethral thermal ablation in the management of benign prostatic hyperplasia," New Frontiers in Medical Device Technology, John Wiley & Sons, New York ,1995,Ch.3, pp. 79-103.
Furer et al., Mechanism and Therapy of Cardiac Arrhythmias in Adults with Congenital Heart Disease. Mt. Sinai J. Medicine 72, 263-69 (2005).
McDaniel et al., Catheter Ablation in Children and Adolescents. Heart and Rhythm 3, 95-101 (2006).
Garreaun et al., Radiofrequency Ablation for Primary and Metastatic Liver Tumors: A Critical Review of the Literature. Amer. J. Surgery 195, 508-20 (2008).
Steinke, Radiofrequency Ablation of Pulmonary Tumors: Current Status, Cancer Imaging 8, 27-35 (2008).
Issa et al., Transurethral Needle Ablation: An Overview of Radiofrequency Thermal Therapy for the Treatment of BPH. Currents Opinions in Urology 6, 20-27 (1996).
Cavaliere et al., Monopolar and Bipolar Radiofrequency Thermal Ablation of Inferior Turbinates: 20 Month Followup. Otolaryngology—Head and Neck Surgery 137, 256-63 (2007).
Arts et al., Influence of Radiofrequency Energy Delivery and the Gastro Esophageal Junction (Stretta Procedure) on Gastroesophageal Reflux Disease. Digestive Diseases and Sciences 52, 2170-7 (2007).
Singh et al., Intradiscal Therapy: a Review of Current Treatment Modalities. Spine 30, 17 Supplement, 520-26 (2005.
Raman et al., A New Type of Secondary Radiation. Nature 121, 501-2 (1928).
Short et al., Development and Preliminary Results of an Endoscopy Raman Probe for Potential in Vivo Diagnosis of Lung Cancers. Optics Letters 33, 711-13 (2008).
Min et al., 1064 nm Near-Infrared Multichannel Raman Spectroscopy of Fresh Human Lung Tissues, Journal of Raman Spectroscopy, 36, 73-76 (2005).
Haka et al., Diagnosing Breast Cancer by Using Raman Spectroscopy. PNAS 102, 12371-12376 (2005).
Motz et al., Optical Fiber Probe for Biomedical Raman Spectroscopy. Applied Optics 43, 542-54 (2004).
Kast et al., Raman Spectroscopy Can Differentiate Malignant Tumors from Normal Breast Tissue and Detect Early Neoplastic Changes in a Mouse Model. Biopolymers 89, 235 241 (2007).
Bao et al., A Prototype Ultrasound-guided Laparascopic Radi Frequency Ablation System, Surgical Endoscopy, 21,74-79 (2007).
Haka et al., In vivo Margin Assesment during Partial Mastectomy Breast Surgery using Raman Spectroscopy, Cancer Research, 2006.
Jong et al., Discrimination between Non-tumor Bladder Tissue and Tumor by Raman Spectroscopy, Anal. Chem., 78, 7761-7769 (2006).
Koenig et al., Autofluorescence Guided Biopsy for the Early Diagnosis of Bladder Carcinoma, Journal of Urology, 159 (6), 1871-1875 (1998).
Koljenovi, Raman Spectroscopic Characterization of Porcine Brain Tissue Using a Single; http://pubs.acs.org/doi/abs/10.1021/ac0616512; Anal. Chem. (2007) 79 (2), pp. 557-564.
Abubaker PhD, Differences in Raman Spectra of Aluminium Treated Brain Tissue Sample; The Internet Journal of Toxicology (2008) vol. 4 No. 2.

* cited by examiner

INTEGRATED FIBER OPTIC RAMAN SPECTROSCOPY AND RADIO FREQUENCY ABLATION

CROSS REFERENCE TO RELATED APPLICATIONS

This application claims the benefit of International Patent Application Serial No. PCT/US10/44438 filed on Aug. 4, 2010. The disclosures of the International Patent Application are hereby incorporated by reference for all purposes.

This application claims the benefit of U.S. Provisional Patent Application Ser. No. 61/237,338 filed on Aug. 27, 2009. The disclosures of the provisional patent application are hereby incorporated by reference for all purposes.

BACKGROUND

Unless otherwise indicated herein, the materials described in this section are not prior art to the claims in this application and are not admitted to be prior art by inclusion in this section.

In detecting diseased tissues such as cancerous tumors, Raman spectroscopy is a non-destructive technique providing both qualitative and quantitative information about examined biological tissues. Compared to non-invasive techniques such as X-ray tomography, ultrasound imaging, and similar ones, Raman spectroscopy can provide a detailed picture of analytical data about tissues and allow for analysis of biological tissues through exposure to a monochromatic light source and measuring the spectral characteristics of the scattered signal. While Raman spectroscopy involves a somewhat invasive method such as use of an endoscopic probe, it is non-destructive compared to surgical techniques like biopsies.

Traditional treatments for tumors such as cancer tumors include surgery, chemotherapy, radiotherapy, and combinations of those. While each of these therapy methods is effective in treating certain forms of cancer, other forms may be resistant to their effects. Moreover, side effects of varying degrees are expected with each therapy form. Targeted therapies are a recent development, which target specific tissues through medication or other methods such as proton radiation or electromagnetically induced heat (hyperthermia). These therapies may reduce side effects while focusing on the diseased tissues.

The present disclosure recognizes that there are many challenges in detecting diseased tissues and subsequently treating them. Tumors may metastasize inside the body, errors in estimating a size and composition of the diseased tissue may result in unnecessary damage to healthy tissues during therapy. Furthermore, subjecting a patient to multiple sessions of invasive detection and therapy procedures (e.g. endoscopy) may increase a risk of ancillary problems such as cardiac stress due to anesthesia, and comparable ones.

SUMMARY

The foregoing summary is illustrative only and is not intended to be in any way limiting. In addition to the illustrative aspects, embodiments, and features described above, further aspects, embodiments, and features will become apparent by reference to the drawings and the following detailed description.

The present disclosure describes a method for applying Radio Frequency (RF) induced hyperthermia in conjunction with fiber optic spectroscopy. The method includes detecting a target tissue by fiber optic spectroscopy employing an endoscopic probe and applying an alternating electromagnetic field from an RF source through the endoscopic probe, where the alternating electromagnetic field is effective to induce heat in the target tissue.

The present disclosure also describes an apparatus configured to apply RF induced hyperthermia in conjunction with fiber optic spectroscopy. Some examples of the apparatus may include a spectroscopy module adapted to provide an optical signal for Raman spectroscopy of a target tissue, an RF module adapted to provide an RF signal configured to induce heat in the target tissue, and an apparatus configured to carry the optical signal and the RF signal to the target tissue as well as probing a temperature of the ablated tissue.

The present disclosure further describes an endoscopic probe for applying RF induced hyperthermia in conjunction with fiber optic spectroscopy. The endoscopic probe includes a center fiber adapted to deliver a laser beam for Raman spectroscopy to a target tissue, a first group of fibers surrounding the center fiber adapted to carry backscattered Raman signal to a spectroscopy module equipped with filters/lenses to enhance received signal, a second group of fibers surrounding the first group of fibers adapted to carry captured visible light to a microscope, a conductive inner shield surrounding the second group of fibers, a third group of fibers surrounding the conductive inner shield adapted to carry visible light to the target tissue, a fourth group of fibers dispersed among the third group of fibers adapted to sense infrared emissions from ablated tissues to a temperature sensing module, and a conductive outer shield surrounding the third group of fibers. The alternating electromagnetic field may be applied to the target tissue for inducing heat by transmitting an RF signal through outer and inner conductive shields configured as a coaxial cable to radiate from the open end of the endoscopic probe.

The present disclosure further describes a computer-readable storage medium having instructions stored thereon for applying Radio Frequency (RF) induced hyperthermia in conjunction with fiber optic spectroscopy. The instructions stored on the computer-readable storage medium may include detecting a target tissue by visual imaging, identifying a composition of the target tissue by Raman spectroscopy and determining whether the target tissue is a tumor based on the composition. If the target tissue is a tumor, the instructions may include applying an alternating electromagnetic field from an RF source through an endoscopic probe by transmitting an RF signal through concentrically constructed outer and inner conductive shields of the endoscopic probe, where the alternating electromagnetic field is effective to induce heat in the tumor. The instructions may further include determining an approximate temperature of the tumor by heat sensing through the endoscopic probe and adjusting one or more of a level and/or a duration of the RF signal in response to the pre-determined temperature.

BRIEF DESCRIPTION OF THE DRAWINGS

The foregoing and other features of this disclosure will become more fully apparent from the following description and appended claims, taken in conjunction with the accompanying drawings. Understanding that these drawings depict only several embodiments in accordance with the disclosure and are, therefore, not to be considered limiting of its scope, the disclosure will be described with additional specificity and detail through use of the accompanying drawings, in which:

DETAILED DESCRIPTION

Figure 1:
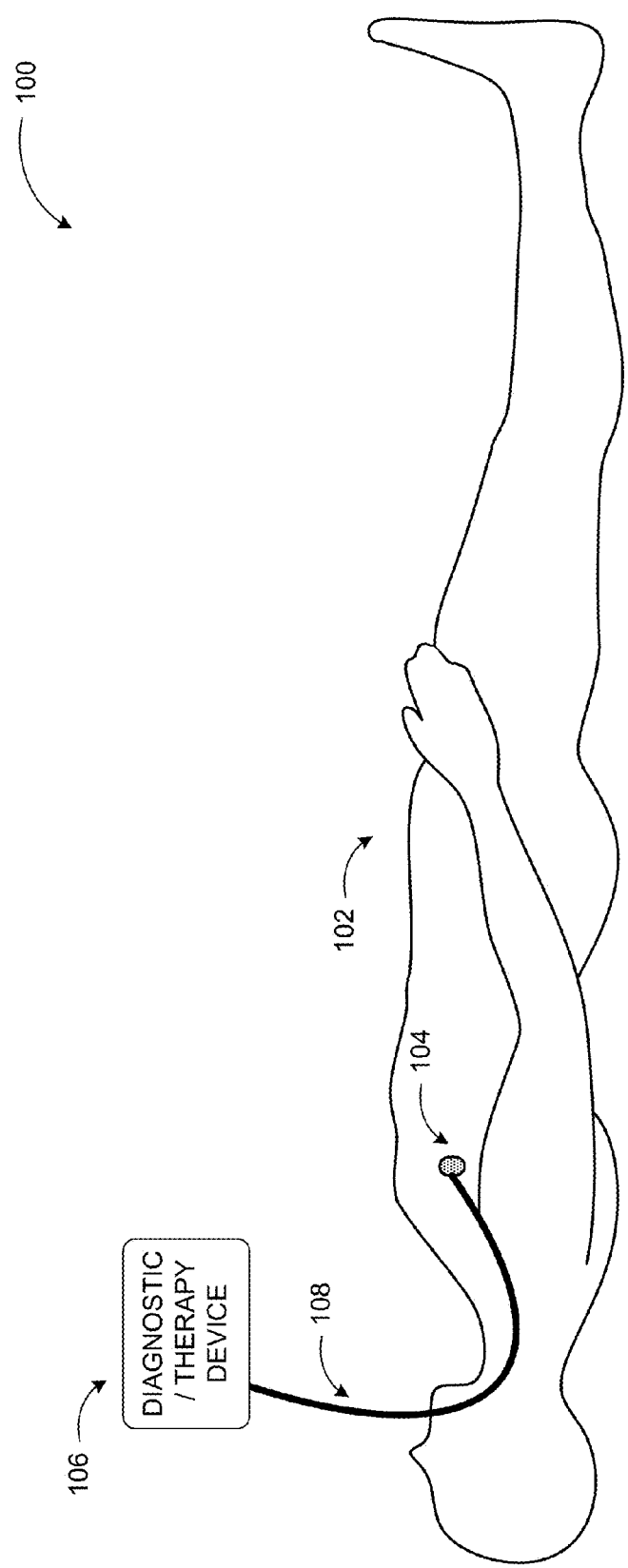
FIG. 1 illustrates use of combined fiber optic spectroscopy and Radio Frequency (RF) induced hyperthermia in a patient for detection and treatment of diseased tissues.

In the following detailed description, reference is made to the accompanying drawings, which form a part hereof. In the drawings, similar symbols typically identify similar components, unless context dictates otherwise. The illustrative embodiments described in the detailed description, drawings, and claims are not meant to be limiting. Other embodiments may be utilized, and other changes may be made, without departing from the spirit or scope of the subject matter presented herein. It will be readily understood that the aspects of the present disclosure, as generally described herein, and illustrated in the Figures, can be arranged, substituted, combined, separated, and designed in a wide variety of different configurations, all of which are explicitly contemplated herein.

This disclosure is generally drawn, inter alia, to methods, apparatus, systems, devices, and/or computer program products related to detecting diseased tissues through Raman spectroscopy and treating the tissues by RF induced hyperthermia in an integrated manner.

Briefly stated, technologies are generally described for detecting diseased tissues through fiber optic based Raman spectroscopy, image acquisition, and/or RF induced hyperthermia treatment of the detected tissues in an integrated manner. A fiber optic bundle for carrying optical and RF signals for the spectroscopy, visual imaging, and RF ablation may also be used to detect a temperature of the treated tissue such that level and duration of the RF signal can be controlled for optimum results. Coaxially configured shielding of the fiber optic bundle may be used to propagate and deliver the RF signal. Sources and detectors for the optical and RF signals may be integrated into an endoscopic probe containing the fiber optic bundle or be externally positioned. An integrated or remote controller may be employed to manage the optical imaging, spectroscopy, RF ablation, and thermal sensing operations.

FIG. 1 illustrates use of combined fiber optic spectroscopy and RF induced hyperthermia in a patient for detection and treatment of diseased tissues according to at least some embodiments described herein. By integrating image acquisition, Raman spectroscopy for analysis of biological tissues, temperature sensing and RF induced hyperthermia in an integrated fiber optic based system, diseased tissues may be identified, analyzed, and treated in a single procedure.

Localized RF induced hyperthermia may be used to destroy diseased tissue in treating a number of illnesses including, but not limited to, cancerous (or non-cancerous) tumors, cardiac malfunctions, sleep apnea, and similar illnesses where destruction of diseases tissue may cure or manage the illness. As shown in diagram 100, a diagnostic/therapy device 106 may house hardware and software components for generating optical signals for visual imaging and Raman spectroscopy, generating RF signals for inducing hyperthermia, detecting reflected/scattered optical signals, detecting infrared emissions for temperature measurement, and controlling various operations. The optical and RF signals may be delivered to a target tissue 104 inside body 102 through a fiber optic bundle 108. One example implementation includes detection and treatment of lung cancer tumors through endoscopic delivery of optical signals and RF signals to the lungs.

Some embodiments are directed to use of RF induced hyperthermia together with Raman spectroscopy in an integrated manner to examine and treat diseased tissues. Raman spectroscopy is employed in cancer diagnosis, and is used to determine a nature of abnormal body tissues in order to differentiate between malignant and benign growths. Raman spectroscopy allows for analysis of biological tissues through image acquisition, by exposing tissue samples to a monochromatic light source and measuring the spectral characteristics of the scattered signal. Raman effect occurs when a laser signal impinges upon a molecule and interacts with the electron cloud and the bonds of that molecule. For the spontaneous Raman effect, a photon excites the molecule from the ground state to a virtual energy state. When the molecule relaxes it emits a photon and it returns to a different rotational or vibrational state. The difference in energy between the original state and this new state leads to a shift in the emitted photon's frequency different from the excitation wavelength. Thus, by detecting wavelengths of the backscattered signal (different from excitation wavelengths), a system according to embodiments may identify which molecules are present and their amounts in the target tissue.

Raman spectroscopy may be applied through an invasive procedure using tools such as endoscopic probes and catheters. After a tissue sample has been determined to be diseased (e.g., malignant tumor), RF induced hyperthermia may be applied through an invasive procedure using an endoscopic probe. When the endoscopic probe is near the targeted abnormal tissue, RF energy may be applied to the tissue resulting in tissue hyperthermia. RF hyperthermia (or RF ablation) is a therapy based on destroying diseased tissues by inducing excessive heat through RF energy in the diseased tissues. The applied RF energy may be converted to heat by water molecules present in the target tissue. Temperatures over approximately 41° C. cause necrosis of tumor tissues, while normal tissues are not destroyed until approximately 48° C. Using this principle, tumors may be heated to a temperature between 41° C. and 48° C. through the RF induced hyperthermia and necrotized while healthy tissue around them is preserved.

Temperature control is an important aspect of induced hyperthermia. Therefore, the target tissue may be monitored during the application of RF induced hyperthermia. For more accurate determination of target tissue temperature, infrared thermal detection through the same system housing the laser/visible light fibers and RF energy delivery mechanism may be used. Thus, an example system for inducing hyperthermia integrated with fiber optic spectroscopy according to some of the embodiments may include a passive thermal sensing apparatus. For example, an infrared (IR) photodiode based detector module may be coupled to one or more IR carrying fibers in the fiber bundle, and used to determine the temperature of the target tissue based on the detected IR emissions. Parameters of the applied RF field such as its magnitude, frequency, and/or duration may be determined/adjusted based on the measured temperature of the target tissue during the RF ablation process. For example, the magnitude of the RF field may be increased to bring the temperature of a tumor to 45° C. from normal body temperature, and the duration of the RF field adjusted to maintain the higher temperature until the tumor is necrotized.

Figure 2:
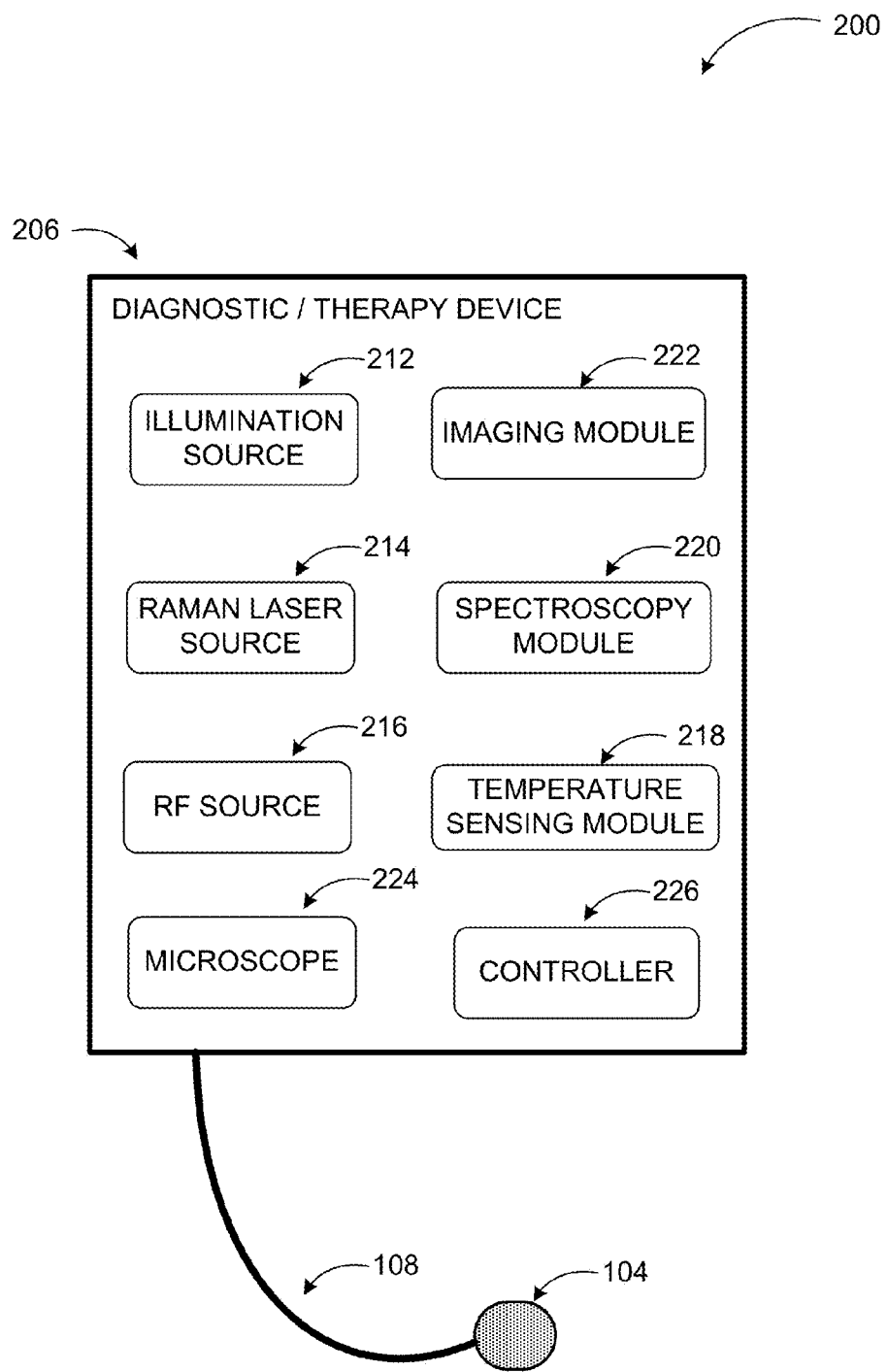
FIG. 2 illustrates a block diagram of an example apparatus for detecting diseased tissues and treating them via RF induced hyperthermia.

FIG. 2 illustrates a block diagram of an example apparatus for detecting diseased tissues and treating them via RF induced hyperthermia. According to some embodiments, a diagnostic/therapy device assembles within a coaxial cable/waveguide geometry a fiber optic system for Raman spectroscopy of target tissues and RF power delivery for diagnosing and treating by ablation diseased tissues in a single diagnostic and surgical instrument. Such a system may be assembled by organizing fibers for different tasks (e.g. illumination light carrying fibers, laser carrying fibers, IR carrying fibers) around a central excitation laser fiber with an inner and outer conductive shield delivering the RF signal. While visual detection of the location of diseased tissue may be performed externally or through another probe, a device according to some embodiments may optionally include a visual imaging aspect as well. Through the visual imaging aspect, the target tissue may be located and examined in visible wavelengths. For example, a color of the target tissue may provide information about whether the target tissue is healthy or not.

Diagram 200 illustrates diagnostic/therapy device 206, endoscopic probe 108 and target tissue 104. Diagnostic/therapy device 206 may include a number of modules for performing various operations. Some of the modules such as the illumination source may be optional. Moreover, some of the operations may be combined in a single module. For example, the laser source may be used for both Raman spectroscopy and illumination. The modules may include, but are not limited to, an illumination source 212 adapted to provide an optical signal for visual imaging (e.g., white light), a laser source 214 adapted to provide a laser signal for Raman spectroscopy, an RF source 216 adapted to provide an RF signal (e.g., in the microwave range frequencies), a temperature sensing module 218 adapted to determine a temperature (e.g., via infrared sensing) of the target tissue while RF induced hyperthermia is being applied, a spectroscopy module 220 adapted to analyze the laser signal backscattered from the target tissue spectrally to determine a composition of the tissue (e.g. types and amounts of molecules within the tissue), and an imaging module 222 adapted to generate a visual image of the target tissue using the reflected light transmitted by the illumination source 212.

Illumination source 212 may include but is not limited to a white light emitting diode (LED), a monochromatic LED, or a light bulb. Laser source 214 may include but is not limited to a solid state laser source such as a laser diode. RF source 216 may include but is not limited to a fixed/variable frequency oscillator/synthesizer with/without a power amplifier. Temperature sensing may be performed externally or internally employing, in a non-limiting example, a fiber based infrared thermometer (e.g. temperature sensing fibers and an IR photodiode/amplifier module).

Diagnostic/therapy device 206 may also include a microscope 224 for enhancing reflected visible light for creating magnified images of the target tissue and/or examining the captured images. As discussed previously, other modules of diagnostic/therapy device 206 such as but not limited to the illumination source and the imaging module may also be optional. Microscope 224 may include but is not limited to a differential interference microscope, a phase contrast microscope, a fluorescent microscope, or a dark field microscope. Controller 226 may be adapted to manage operations of the different modules including but not limited to controlling their timing and operational parameters. For example, controller 226 may adjust a frequency and magnitude of the visible light and laser signal by interacting with the illumination source 212 and laser source 214. Furthermore, controller 226 may adjust characteristics of the RF signal such as but not limited to level, duration, frequency, modulation, and similar ones based on measured temperature. Controller 226 may also manage interaction with external devices such as but not limited to data storage or output devices (e.g., a printer, a display) to provide information to human operators. Input in form of direct input (e.g., through a keyboard) and/or pre-programming may be provided to controller 226 for the diagnostic and therapy procedures. A system according to embodiments may include any of the components listed herein, but is not limited to all of the components or a particular order.

Endoscopic probe 108 may include a fiber optic bundle with different layers of fibers for carrying the visible and laser signals to the target tissue and reflected/scattered signals back to the analysis modules, as well as infrared emissions for the temperature sensing module 218. The fiber optic bundle of the endoscopic probe 108 may be utilized as a waveguide or as a coaxial cable to deliver the RF signal from the RF source 216 to target tissue 104. The functionalities of diagnostic/therapy device 206 described herein may be performed by individual hardware, software, or combination of hardware/software modules. Furthermore, two or more of the functionalities (e.g., visual imaging and infrared based temperature sensing) may be performed by a single module). Thus, the components and configurations discussed above are for illustration purposes only and do not constitute a limitation on embodiments.

Figure 3:
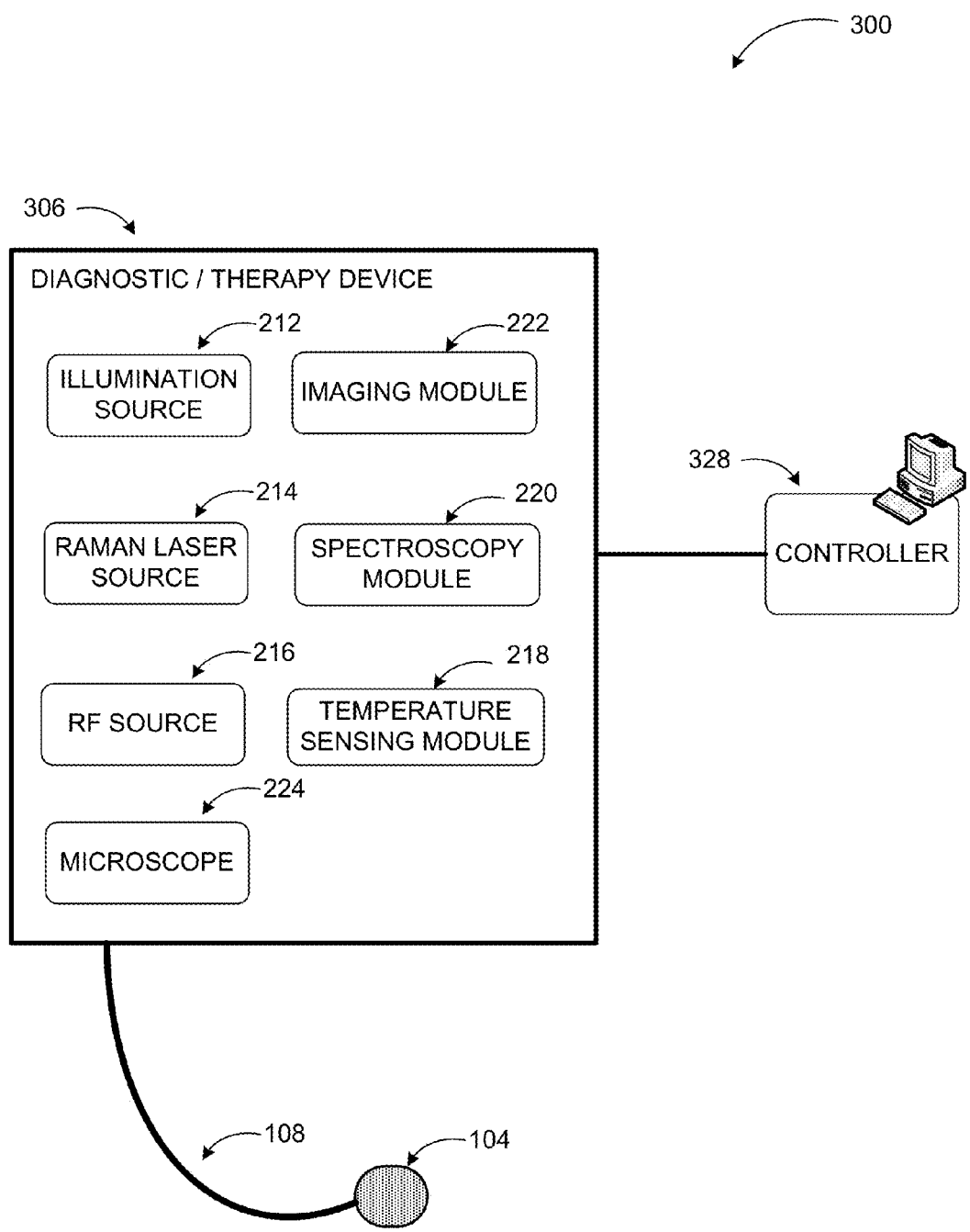
FIG. 3 illustrates a block diagram of another example apparatus for detecting diseased tissues and treating them via RF induced hyperthermia with a remote controller.

FIG. 3 illustrates a block diagram of another example apparatus for detecting diseased tissues and treating them via RF induced hyperthermia with a remote controller. Diagram 300 shows diagnostic/therapy device 306, which is similar to the diagnostic/therapy device 206 of FIG. 2 with similar components. Differently from diagram 200 of FIG. 2, the diagnostic/therapy device 306 is coupled to a remote controller 328.

Remote controller 328 may be a general purpose computing device executing one or more control applications, a special purpose processor, or similar control device. Remote controller 328 may be coupled to diagnostic/therapy device 306 through wired or wireless connection(s) (e.g., RF communication, optical communication), and manage operational aspects of individual modules and receive data from the analysis modules such as, but not limited to, spectroscopy module 220, temperature module 218, and imaging module 222.

In an example operation, initial parameters such as but not limited to spectral bandwidth, and magnitude for the visual imaging light and/or Raman laser excitation may be preprogrammed and/or provided by a human operator to diagnostic/therapy device 306. Illumination source 212 may first transmit visible light. The light reflected from the target tissue 104 may be magnified by microscope 224 or a visual image of the target tissue generated by imaging module 222. In addition to generating the visual image, imaging module 222 may also be used to estimate a size of the target tissue. Based on the visual input, the Raman laser source 214 may be activated illuminating the target tissue with a specific wavelength laser excitation. The backscattered Raman signal may be analyzed by spectroscopy module 220 determining a composition, density, etc. of the target tissue based on spectral analysis. Acquiring Raman spectra from target tissue, spectroscopy module 220 may generate images showing the location and amount of different components. For example, distribution of cholesterol, proteins, nucleic acids, and fatty acids may be determined. More complicated signal- and image-processing techniques may be used to detect or ignore the presence of water, proteins, or other interferents. Based on the analysis results a determination may be made by the controller 328 or by a human operator that the target tissue is diseased tissue (e.g., a tumor), and the RF source 216 activated with an initial level, frequency, and modulation of RF signal for inducing hyperthermia in the target tissue 104.

While the target tissue is being heated by the RF signal, its temperature may be sensed by the temperature sensing module employing infrared emissions. If the temperature needs to be increased or decreased, one or more of the RF signal's parameters may be adjusted by the controller 328 through interaction with RF source 216, and the RF signal may be transmitted with new parameters until the procedure is completed.

Figure 4:
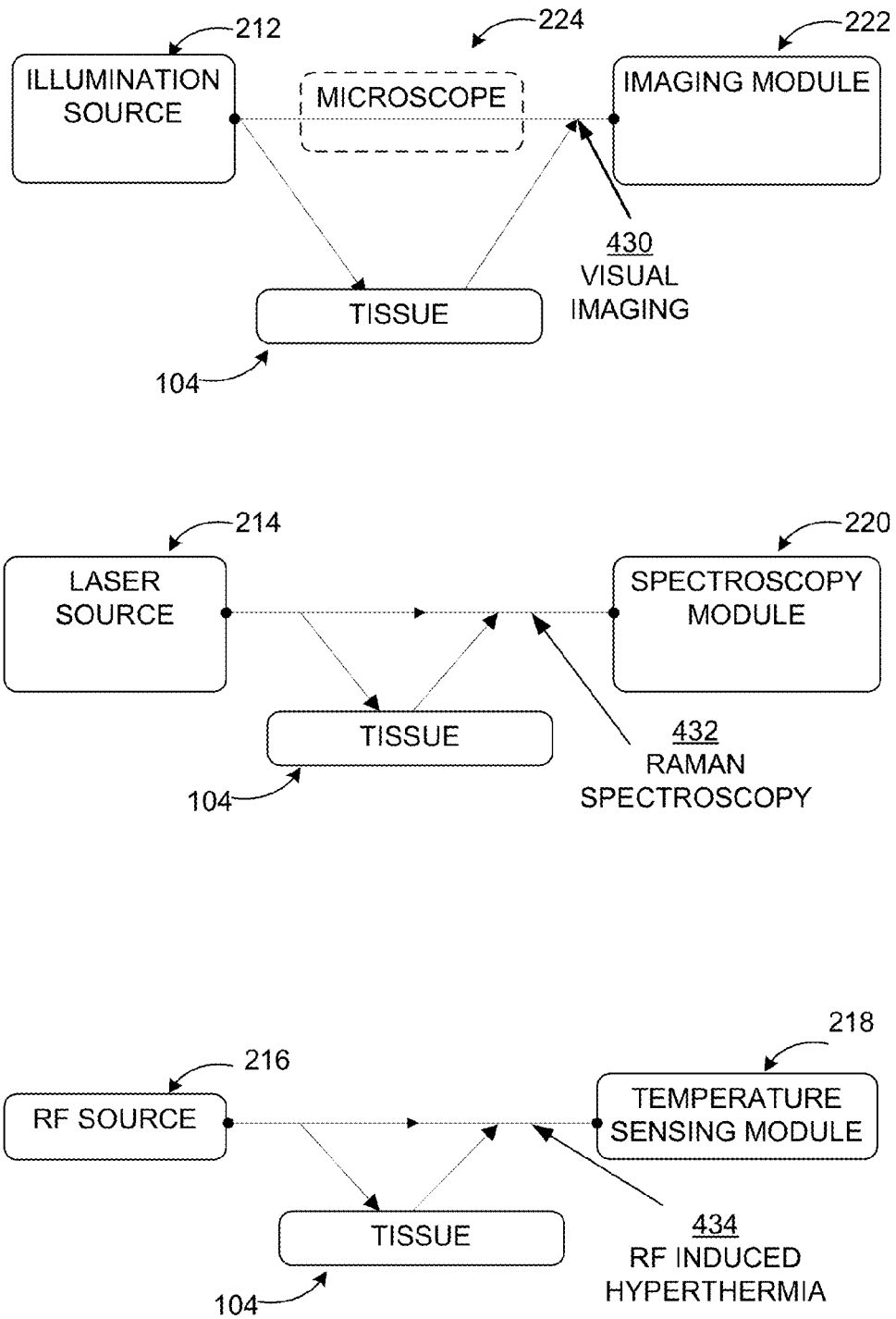
FIG. 4 illustrates interactions between different modules of a system for detecting diseased tissues and treating them via RF induced hyperthermia.

FIG. 4 illustrates interactions between different modules of a system for detecting diseased tissues and treating them via RF induced hyperthermia. As discussed above, illumination source 212 provides visible light for visual imaging 430 by the imaging module 222. The reflected light may be magnified by a microscope 224 for enhanced imaging of the target tissue. The visible light may be white light or a filtered portion of the visible light spectrum depending on desired imaging, tissue type, the environment surrounding the tissue, and comparable factors.

Laser source 214 provides the excitation signal for Raman spectroscopy 432 based on backscattered signal from the target tissue to the spectroscopy module 220. Various wavelengths of lasers may be utilized for the spectroscopy. The wavelengths may typically range from about 400 nm to 1600 nm, but other wavelengths may also be used. According to some embodiments, the laser may be monochromatic. According to other embodiments, multiple wavelengths may be used simultaneously.

The interaction between RF source 216 and temperature sensing module 218 is through the RF induced hyperthermia 434. RF source 216 may transmit an RF signal to induce heat in the target tissue. A frequency of the RF signal may be selected based on a composition of the target tissue, a time needed to complete the ablation procedure, and similar factors. For example, microwave range (around 2.4 GHz) may be selected for heating soft tumors in a short period of time. Temperatures over approximately 41° C. cause necrosis of tumor tissues, while normal tissues are not destroyed until approximately 48° C. Thus, temperature ranges starting around 40° C. may be selected for heat induced by the RF signal. The period of RF ablation application may also be selected based on the desired amount of heat energy to be transferred to the diseased tissue. Repeated 30-90 second applications are one example. Other examples may include a prolonged continuous period (e.g. several minutes), or repeated application periods with different durations (e.g. 20 seconds, 100 seconds, and similar periods). Similarly, a power level of the RF signal may also be adjusted up or down based on whether a desired ablation temperature is achieved at the target tissue. The RF signal may be modulated or continuous wave (CW). Once hyperthermia is induced at the target tissue, the temperature of the tissue may be measured by temperature sensing module 218 employing infrared sensing or a comparable method. Based on the measured temperature (or rate of temperature increase), the amplitude, modulation, and/or duration of the RF signal may be modified to achieve the desired result (ablation of the target tissue).

Figure 5:
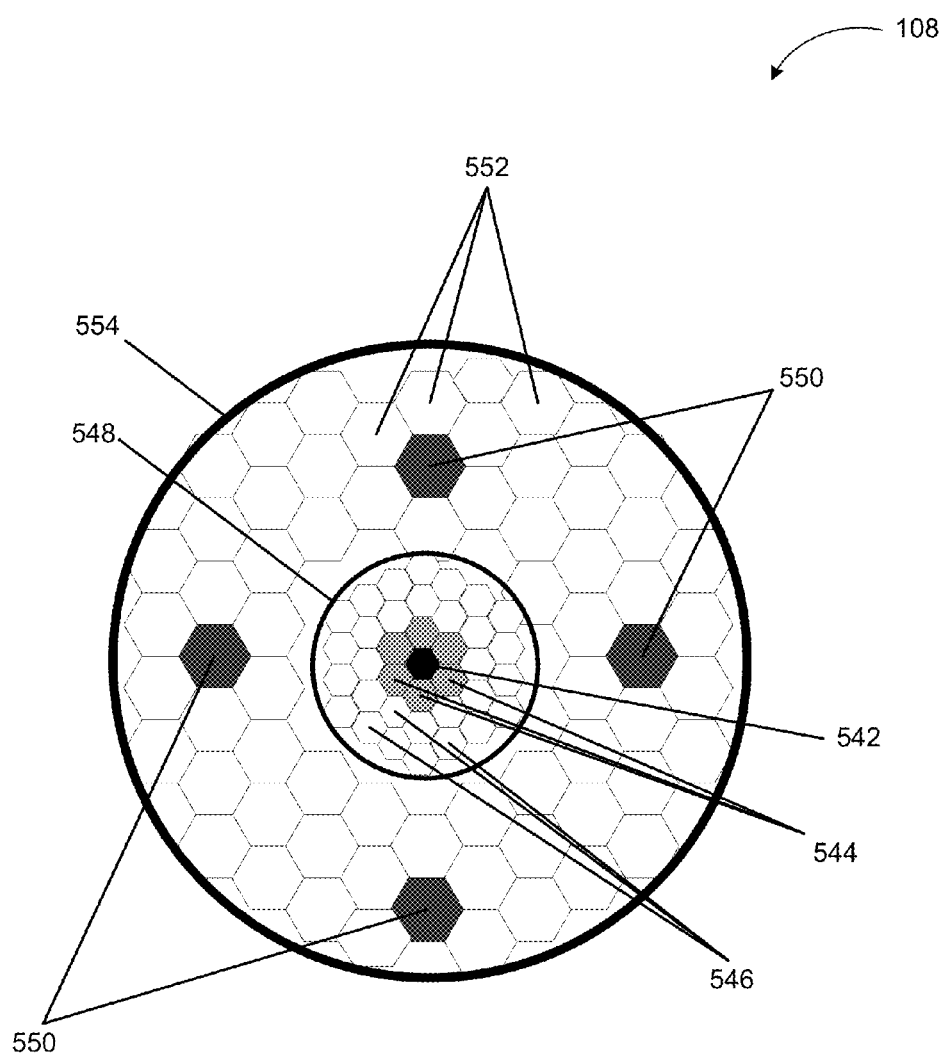
FIG. 5 illustrates a transverse cross section of an endoscopic probe for carrying optical and RF signals in a system adapted to detect diseased tissues and treat them via RF induced hyperthermia.

FIG. 5 illustrates a transverse cross section of an endoscopic probe 108 for carrying optical and RF signals in a system adapted to detect diseased tissues and treat them via RF induced hyperthermia. The fiber optic bundle of the endoscopic probe 108 may be built as a single open ended coaxial cable with an outer diameter ranging from about 0.1 mm to about 10 mm. The diameter of the bundle depends on a number and thickness of the fibers in the bundle. Thus, 0.1 mm may constitute a practical lower limit, while the upper limit may exceed 10 mm. A practical upper limit for the diameter may be set by dimensions the inner and outer shields acting as a waveguide or coaxial cable in delivering the RF signal. To provide an efficient waveguide or coaxial cable, the diameter may be determined based on a frequency used. For example, embodiments using microwave frequency ranges may use approximately 10 mm as an upper limit, while the diameter may be larger for lower frequencies (e.g. 20-30 mm). A length of the bundle may vary depending on the application. The length may vary from a few centimeters to tens of meters.

The probe may be designed to integrate one or more IR temperature sensors, optical fibers for Raman spectroscopy, and visual light imaging in a coaxial cable suitable for delivery of RF power. At the center of the bundle may be the Raman excitation fiber 542 carrying the excitation signal from a laser source for spectroscopy. The Raman excitation fiber 542 may be surrounded by Raman backscattered laser collection fibers 544. The Raman backscattered laser collection fibers 544, in turn may be surrounded by leached fiber bundle 546 for imaging (i.e., for collection of reflected visible light from target tissue). Leached fiber bundles are flexible, coherent image guides that are built by multiple draws of a high index core glass, with a lower index clad glass and an acid-soluble jacket glass. Different types of fibers for carrying laser signal (Raman excitation, Raman laser collection) and illumination light are well known in the art and not described in detail herein. A metalized shield 548 may surround the leached fibers 546. Metalized shield 548 may include a conductive sheet (e.g. copper, copper alloys, and similar metals) or a non-conductive flexible material covered with conductive material (e.g. a plastic sheet sprayed on with a metal). Any metal that provides sufficient conductivity to reduce wall losses for guiding RF energy to the diseased tissue may be employed.

The metalized shield 548 may act as the center conductor of the coaxial cable carrying the RF signal for inducing hyperthermia. A second metalized shield 554, concentric with the first metalized shield 548, may envelope the entire bundle acting as the outside shield of the coaxial cable.

According to other embodiments, visible light illumination fibers 552 may be positioned between the two metalized shields carrying the visible light to the target tissue. The fiber bundle may contain from a few hundred to a few ten thousand fibers packed in a flexible cylindrical configuration. An outer diameter of the endoscopic probe may range between about 1 mm and about 10 mm depending on the number and size of the fibers and the conductive shields as discussed above. A diameter of the approximately circularly assembled Raman backscattered laser collection fibers may range between about 0.5 mm and about 2 mm.

According to further embodiments, a number of IR sensing fibers 550 may be dispersed among the illumination fibers 552. The IR sensing fibers 550 may be adapted to carry infrared emissions from the heated target tissue to a temperature sensing module for measurement of the temperature of the target tissue.

Figure 6:
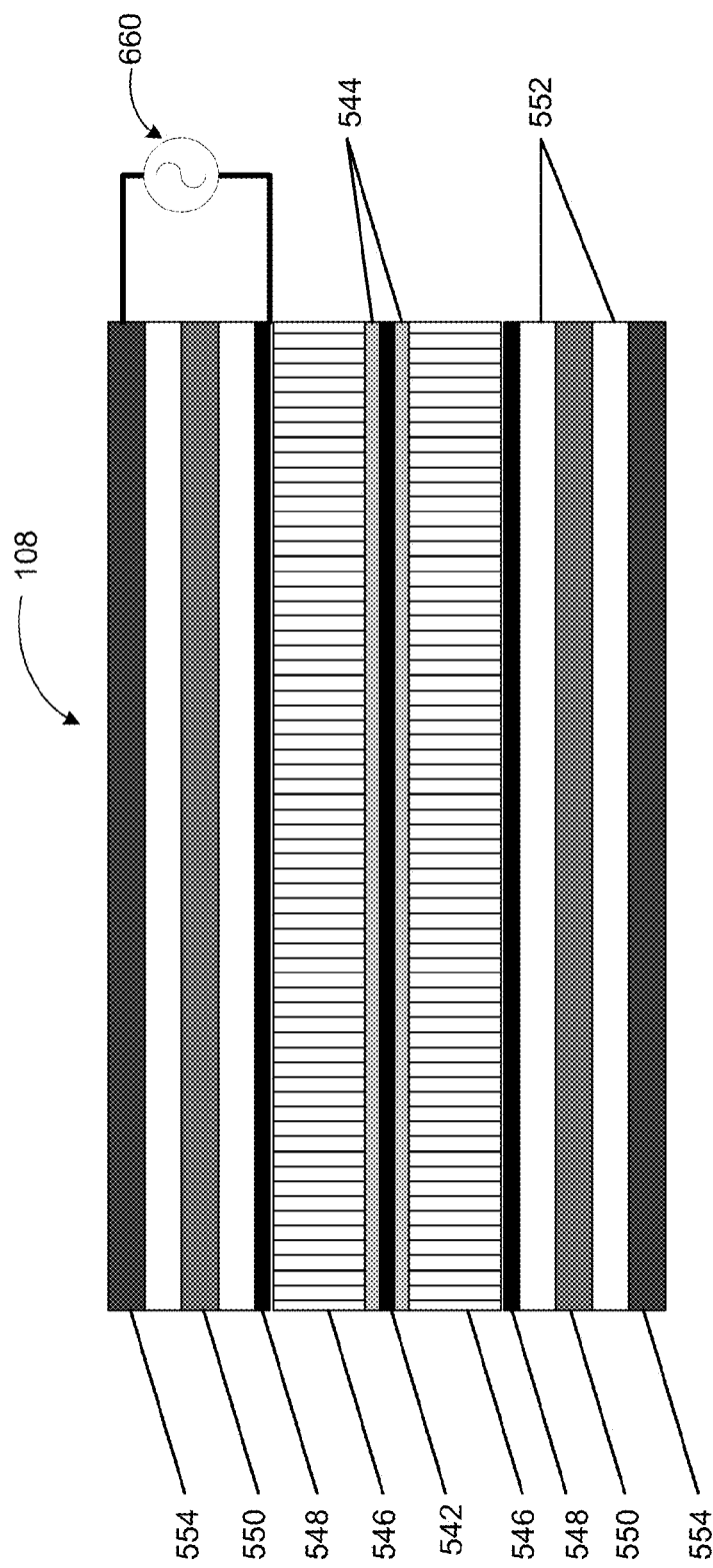
FIG. 6 illustrates a longitudinal cross section of an endoscopic probe for carrying optical and RF signals in a system adapted to detect diseased tissues and treat them via RF induced hyperthermia.

FIG. 6 illustrates a longitudinal cross section of an endoscopic probe for carrying optical and RF signals in a system adapted to detect diseased tissues and treat them via RF induced hyperthermia. In a system setting, an RF source 660 may be coupled between the outer metalized shield 554 and inner metalized shield 548 transmitting the RF signal through the fiber bundle acting as a coaxial cable. RF source 660 may be any RF signal generator backed up with/without power amplifier. IR sensing fibers 550 may be coupled to an IR thermometer for measuring the temperature of the target tissue. An IR thermometer may include a lens to focus the infrared energy on to a detector (e.g. an IR photodiode), which converts the energy to an electrical signal that can be measured corresponding to change of temperature at the target tissue.

A visible light source (e.g. a light emitting diode, a bulb) may be coupled to the imaging illumination fibers 552 propagating the illumination light to the target tissue. Similarly, Raman excitation fiber 542 at the center may be coupled to a laser source such as but not limited to a laser diode and carry the excitation signal to the target tissue. While a laser signal may be obtained from a variety of sources such as gas lasers, chemical lasers, excimer lasers, or solid state lasers, a laser diode (solid state laser source) may be a practical laser source for some embodiments. Raman excitation fiber 542 may also include one or more laser filters to eliminate unwanted laser background, scatter, and plasma in order to optimize signal-to-noise ratio. Laser filters may include, but are not limited to, laser line filters, laser edge filters, and laser rejection filters as well as lenses to enhance received Raman signal. Raman backscattered laser collection fibers 544 may be coupled to the spectroscopy module for collection of backscattered laser from the target tissue. Leached fibers 546 may be coupled to an image capturing device such as but not limited to a Complementary Metal-Oxide Semiconductor (CMOS) detector, a Charge Coupled Device (CCD) device, a photodiode detector, a photomultiplier tube (PMT), and similar cameras for capturing images of the target tissue.

Figure 7:
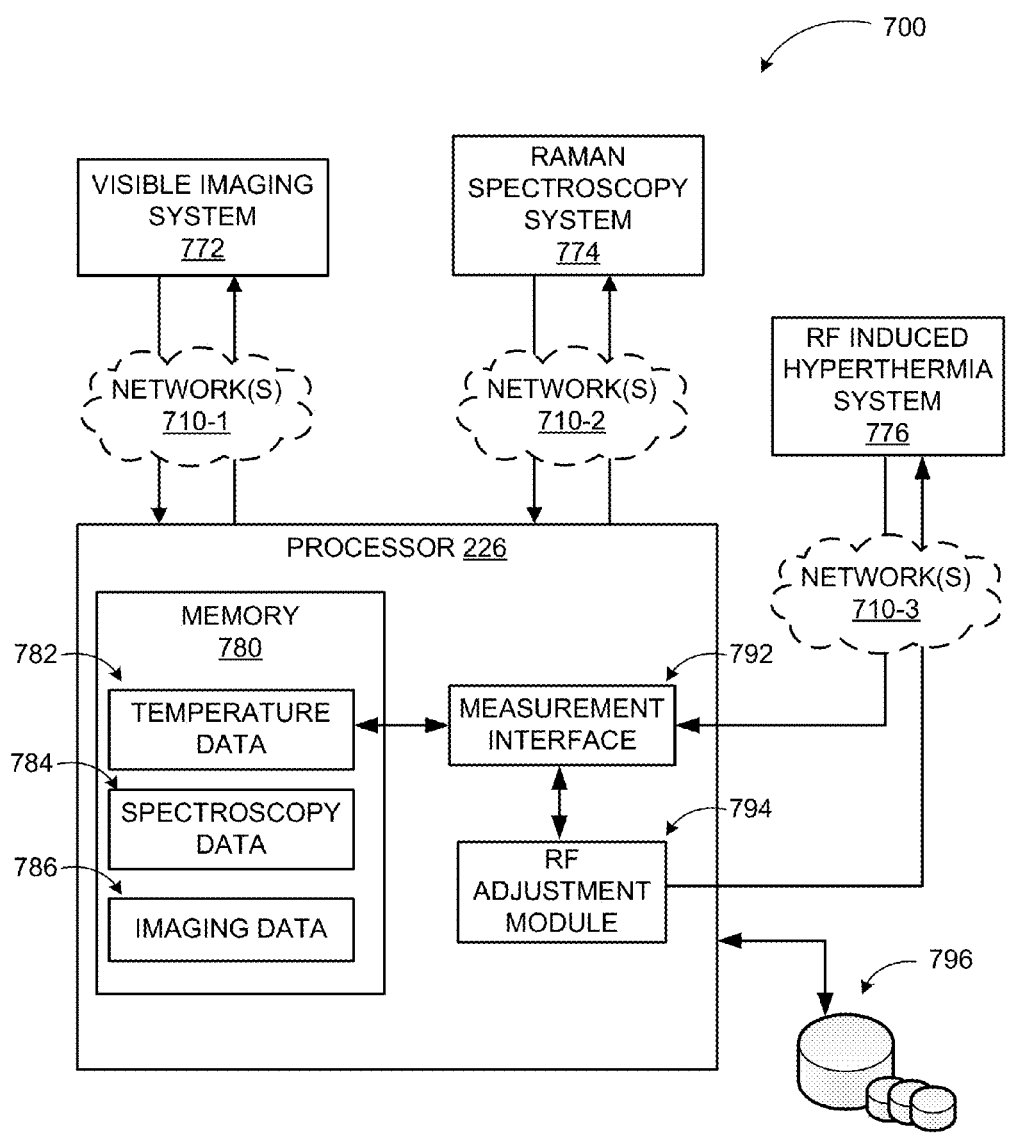
FIG. 7 illustrates a special purpose processor, which may be used to implement integrated fiber optic spectroscopy and RF ablation.

FIG. 7 illustrates a special purpose processor, which may be used to implement integrated fiber optic spectroscopy and RF ablation according to at least embodiments described herein. Integrated fiber optic spectroscopy and RF ablation system 700 can be, for example, as described in FIG. 2 or 3. Processor 226 may include special modules such as measurement interface module 792 and RF signal control module 794. These modules may employ data acquisition including, but not limited to, temperature data 782, spectroscopy data 784, and imaging data 786, which may be stored in memory 780 or according to other embodiments in remote data stores 796. Processor 226 may be configured interact with visible imaging systems 772, Raman spectroscopy system 774, and RF induced hyperthermia system 776 through operable coupling (wired or wireless) or through networks 710-1, 710-2, and 710-3, respectively. The communications may also be established over the same network(s). By executing instructions for its special modules, processor 226 may control operational parameters of the integrated fiber optic spectroscopy and RF ablation system 700 operable coupling (wired or wireless) or through networks 710-1, 710-2, and 710-3.

While embodiments have been discussed above using specific examples, components, and configurations, they are intended to provide a general guideline to be used for inducing controlled hyperthermia through an RF field applied through a fiber optic bundle carrying optical signals for Raman spectroscopy and/or visual imaging. These examples do not constitute a limitation on the embodiments, which may be implemented using other components, diseased tissue detection, RF induction, or temperature measurement schemes, and/or configurations using the principles described herein.

Figure 8:
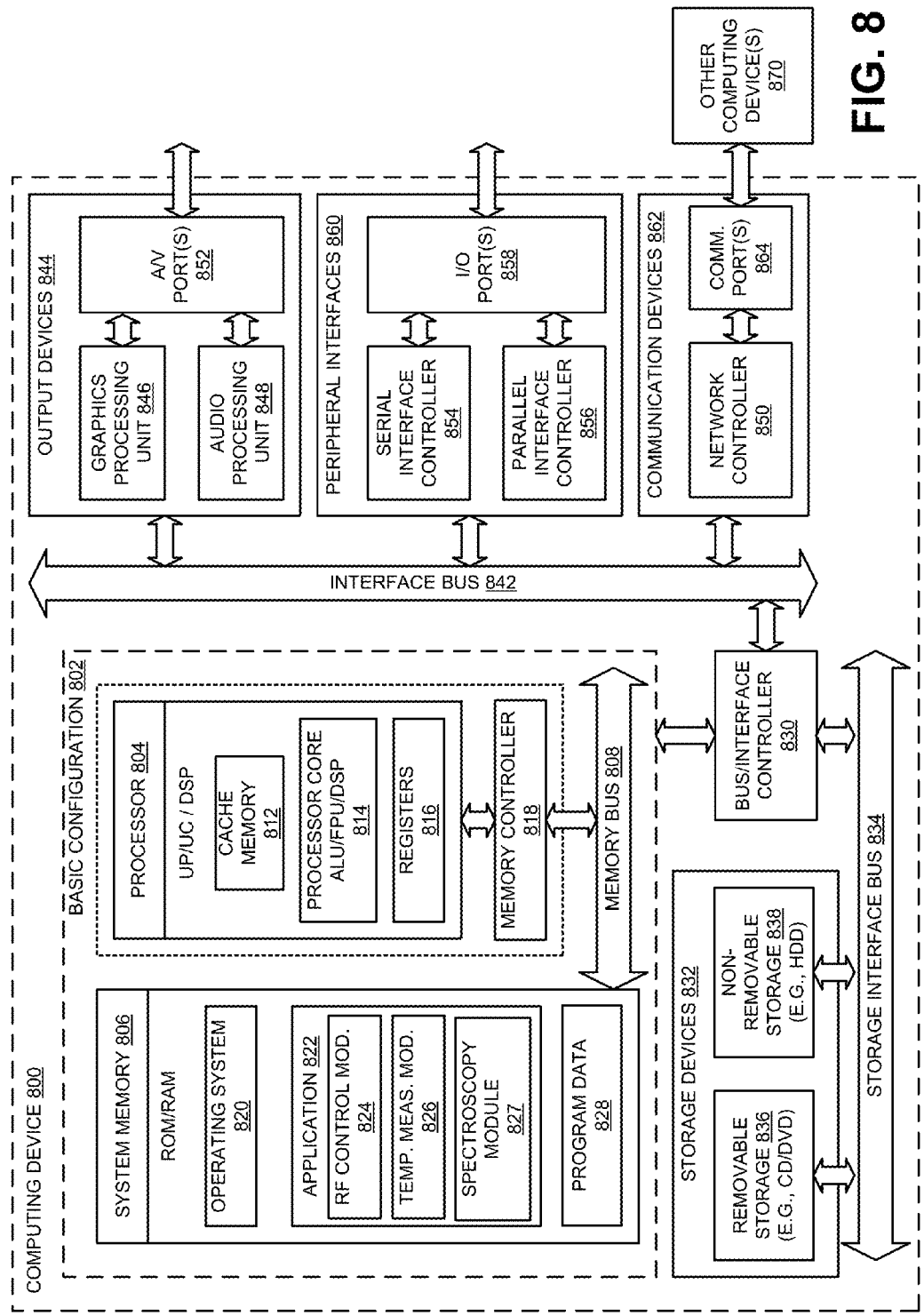
FIG. 8 illustrates a general purpose computing device, which may be used to control an integrated fiber optic spectroscopy and RF ablation system.

FIG. 8 illustrates a general purpose computing device 800, which may be adapted to control an example fiber optic spectroscopy and RF ablation system that is arranged according to at least some embodiments of the present disclosure. General purpose computing device 800 may be employed to control various operational parameters of illumination, laser, and RF sources; visible light, laser, and RF detectors; and any auxiliary devices such as power sources for individual operational modules. For example, a level, a duration, and/or a frequency of the RF signal may be adjusted based on measured temperature of the target tissue by computing device 800 through controlling operational parameters of the RF source. In a very basic configuration 802, computing device 800 typically includes one or more processors 804 and a system memory 806. A memory bus 808 may be used for communicating between processor 804 and system memory 806.

Depending on the desired configuration, processor 804 may be of any type including but not limited to a microprocessor (μP), a microcontroller (μC), a digital signal processor (DSP), or any combination thereof. Processor 804 may include one more levels of caching, such as a level cache memory 812, a processor core 814, and registers 816. Example processor core 814 may include an arithmetic logic unit (ALU), a floating point unit (FPU), a digital signal processing core (DSP Core), or any combination thereof. An example memory controller 818 may also be used with processor 804, or in some implementations memory controller 818 may be an internal part of processor 804.

Depending on the desired configuration, system memory 806 may be of any type including but not limited to volatile memory (such as RAM), non-volatile memory (such as ROM, flash memory, etc.) or any combination thereof System memory 806 may include an operating system 820, one or more applications 822, and program data 828. Application 822 may include an RF control module 824 that is arranged to adjust operational parameters of an RF source for inducing hyperthermia in diseased tissues as discussed above. Application 822 may also include a temperature measurement module 826 that is arranged to determine a temperature of the tissue for controlling a level, duration, and other parameters (e.g. frequency or modulation) of the RF signal. Application 822 may also include a spectroscopy module 827 that is arranged to determine a composition of the target tissue to decide whether the tissue is diseased or not. Program data 828 may include any data associated with controlling the spectroscopy, thermal sensing, and RF ablation operations as discussed above (e.g., FIGS. 2, 3, and 4). In some embodiments, application 822 may be arranged to operate with program data 828 on operating system 820 such that fiber optic spectroscopy and RF ablation may be controlled as described herein. This described basic configuration 802 is illustrated in FIG. 8 by those components within the inner dashed line.

Computing device 800 may have additional features or functionality, and additional interfaces to facilitate communications between basic configuration 802 and any required devices and interfaces. For example, a bus/interface controller 830 may be used to facilitate communications between basic configuration 802 and one or more data storage devices 832 via a storage interface bus 834. Data storage devices 832 may be removable storage devices 836, non-removable storage devices 838, or a combination thereof Examples of removable storage and non-removable storage devices include magnetic disk devices such as flexible disk drives and hard-disk drives (HDD), optical disk drives such as compact disk (CD) drives or digital versatile disk (DVD) drives, solid state drives (SSD), and tape drives to name a few. Example computer storage media may include volatile and nonvolatile, removable and non-removable media implemented in any method or technology for storage of information, such as computer readable instructions, data structures, program modules, or other data.

System memory 806, removable storage devices 836 and non-removable storage devices 838 are examples of computer storage media. Computer storage media includes, but is not limited to, RAM, ROM, EEPROM, flash memory or other memory technology, CD-ROM, digital versatile disks (DVD) or other optical storage, magnetic cassettes, magnetic tape, magnetic disk storage or other magnetic storage devices, or any other medium which may be used to store the desired information and which may be accessed by computing device 800. Any such computer storage media may be part of computing device 800.

Computing device 800 may also include an interface bus 842 for facilitating communication from various interface devices (e.g., output devices 844, peripheral interfaces 860, and communication devices 862) to basic configuration 802 via bus/interface controller 830. Example output devices 844 include a graphics processing unit 846 and an audio processing unit 848, which may be configured to communicate to various external devices such as a display or speakers via one or more A/V ports 852. Example peripheral interfaces 860 include a serial interface controller 854 or a parallel interface controller 856, which may be configured to communicate with external devices such as input devices (e.g., keyboard, mouse, pen, voice input device, touch input device, etc.) or other peripheral devices (e.g., printer, scanner, etc.) via one or more I/O ports 858. An example communication device 546 includes a network controller 850, which may be arranged to facilitate communications with one or more other computing devices 870 over a network communication link via one or more communication ports 864.

The network communication link may be one example of a communication media. Communication media may typically be embodied by computer readable instructions, data structures, program modules, or other data in a modulated data signal, such as a carrier wave or other transport mechanism, and may include any information delivery media. A "modulated data signal" may be a signal that has one or more of its characteristics set or changed in such a manner as to encode information in the signal. By way of example, and not limitation, communication media may include wired media such as a wired network or direct-wired connection, and wireless media such as acoustic, radio frequency (RF), microwave, infrared (IR) and other wireless media. The term computer readable media as used herein may include both storage media and communication media.

Computing device 800 may be implemented as a portion of a small-form factor portable (or mobile) electronic device such as a cell phone, a personal data assistant (PDA), a personal media player device, a wireless web-watch device, a personal headset device, an application specific device, or a hybrid device that include any of the above functions. Computing device 800 may also be implemented as a personal computer including both laptop computer and non-laptop computer configurations. Moreover computing device 800 may be implemented as a networked system or as part of a general purpose or specialized server.

Figure 9:
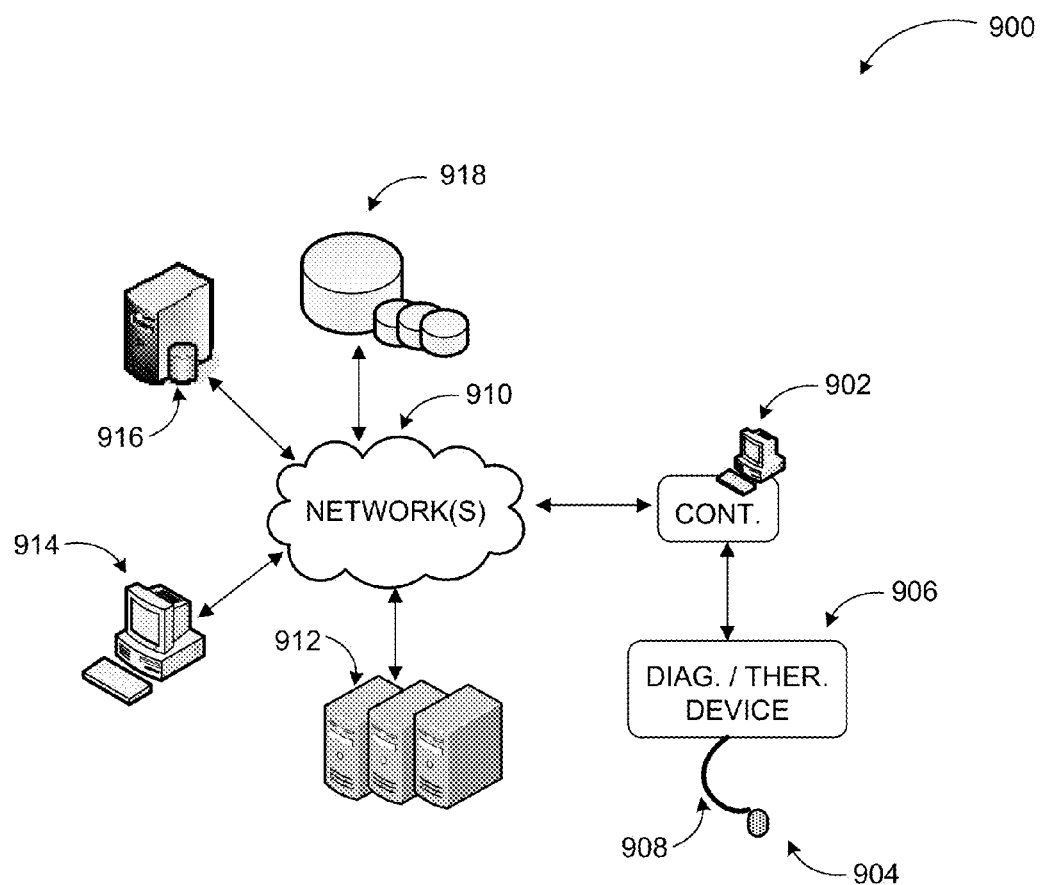
FIG. 9 illustrates a networked environment, where an integrated fiber optic spectroscopy and RF ablation system may be implemented.

FIG. 9 illustrates a networked environment, where an integrated fiber optic spectroscopy and RF ablation system may be implemented in accordance with at least some embodiments described herein. A control system managing fiber optic spectroscopy and RF ablation may be implemented through separate applications, one or more integrated applications, one or more centralized services, or one or more distributed services on one more computing devices. Diagram 900 illustrates an example of a distributed system implementation through networks 910.

As discussed previously, visual imaging, spectroscopy, RF ablation, and thermal sensing operations may be controlled by a local controller 902. Diagnostic and therapy device 906 may provide some of the controls and/or data collection for the operations through endoscopic probe 908, which may be inserted into a patient's body to reach diseased tissue 904. Controller 902 (e.g. a general purpose computing device) may be configured to collect spectroscopy data, visual imaging data, apply RF field for hyperthermia treatment, collect temperature data, provide feedback to an RF source, and/or provide feedback information to an application or service executed on computing device 914 or one or more of the servers 912 through network(s) 910. The application or service may be adapted to manage one or more of spectroscopy/hyperthermia induction systems, maintain patient data, provide initial configuration information to controller 902, and perform similar tasks. Patient data and other data associated with the operation of hyperthermia induction system may be stored in one or more data stores such as data stores 918 and be directly accessible through network(s) 910. Alternatively, data stores 918 may be managed by a database server 916.

Network(s) 910 may comprise any topology of servers, clients, switches, routers, modems, Internet service providers (ISPs), and any appropriate communication media (e.g., wired or wireless communications). A system according to embodiments may have a static or dynamic network topology. Network(s) 910 may include a secure network such as an enterprise network (e.g., a LAN, WAN, or WLAN), an unsecure network such as a wireless open network (e.g., IEEE 802.11 wireless networks), or a world-wide network such as (e.g., the Internet). Network(s) 910 may also comprise a plurality of distinct networks that are adapted to operate together. Network(s) 910 can be configured to provide communication between the nodes described herein. By way of example, and not limitation, network(s) 910 may include wireless media such as acoustic, RF, infrared and other wireless media. Furthermore, network(s) 910 may be portions of the same network or separate networks.

Example embodiments may also include methods. These methods can be implemented in any number of ways, including the structures described herein. One such way is by machine operations, of devices of the type described in the present disclosure. Another optional way is for one or more of the individual operations of the methods to be performed in conjunction with one or more human operators performing some of the operations while other operations are performed by machines (e.g., devices adapted to perform operations). Human operators need not be collocated with each other, but instead can be located about a machine that performs a portion of the overall program or process. In other examples, the human interaction can be automated such as by pre-selected criteria that are machine automated.

Figure 10:
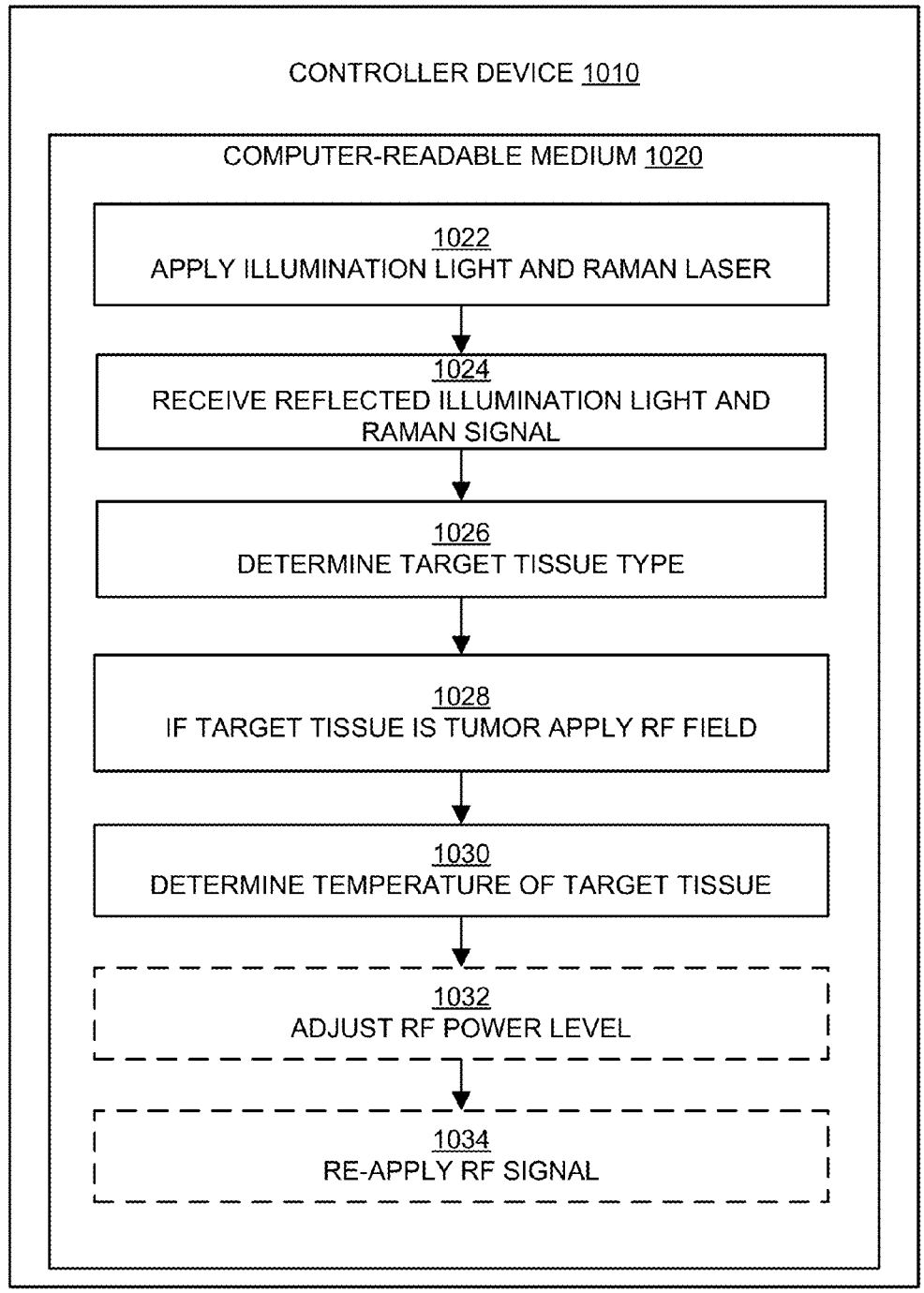
FIG. 10 illustrates a block diagram of an example controller for performing an example method through a computing device.

FIG. 10 illustrates a block diagram of an example controller device 1010 for performing an example method through a computing device (e.g., processor 226 in FIG. 7), arranged in accordance with at least some embodiments of the present disclosure. In some examples, as shown in FIG. 10, computer readable medium 1020 may include machine readable instructions that, when executed by a computing device (e.g., controller device 1010) adapt the computing device to provide at least a portion of the functionality described above with respect to FIG. 2 through FIG. 4. For example, referring to controller device 1010, one or more modules of controller device 1010 may be configured to undertake one or more of the operations shown in FIG. 10.

A process of controlling combined fiber optic spectroscopy and RF ablation may begin with operation 1022, "APPLY ILLUMINATION LIGHT AND RAMAN LASER." At operation 1022, a visual wavelength optical signal and a laser signal may be applied to a target tissue through a fiber optic bundle by an illumination source (e.g., illumination source 212) and a laser source (e.g., laser source 214) with control parameters provided by a controller (e.g., controller 226).

Operation 1022 may be followed by operation 1024, "RECEIVE REFLECTED ILLUMINATION LIGHT AND RAMAN SIGNAL." At operation 1024, reflected optical signals may be received at an imaging module and a spectroscopy module (e.g., imaging module 222 and spectroscopy module 220, respectively). The received signals may be pre-processed (e.g. filtered) and processed for generating a visual image of the target tissue and determining a composition of the target tissue.

Operation 1024 may be followed by operation 1026, "DETERMINE TARGET TISSUE TYPE." At operation 1026, a determination may be made as to whether the target tissue is diseased tissue requiring treatment or not. Additionally, a size, density, and other characteristics of the target tissue may also be determined. The determinations may be made by the respective imaging and spectroscopy modules (e.g. 222 and 220, respectively) or by a controller based on data provided by the imaging and spectroscopy modules.

Operation 1026 may be followed by operation 1028, "IF TARGET TISSUE IS TUMOR, APPLY RF FIELD." At operation 1028, an RF signal may be transmitted by an RF source (e.g., RF source 216) through the fiber optic bundle (e.g., using the shielding of the fiber optic bundle as a waveguide) and hyperthermia induced at the target tissue. A level, duration, frequency, modulation, and similar characteristics of the RF field may be determined by the controller based on tissue type, size, density, etc.

Operation 1028 may be followed by operation 1030, "DETERMINE TEMPERATURE OF TARGET TISSUE." At operation 1030, the temperature of the target tissue as it is being subjected to RF ablation may be determined (e.g., via infrared signals detected by temperature sensing module 218). According to some embodiments, calibration measurements may be performed by the temperature measurement module prior to actual hyperthermia treatment.

Operation 1030 may be followed by optional operation 1032, "ADJUST RF POWER LEVEL." At operation 1032, parameters of applied RF signal for inducing hyperthermia may be adjusted based on feedback obtained from the measured temperature. This may be accomplished manually or by an automated process controller such via one or more of controller 226 of FIG. 2.

Optional operation 1032 may be followed by optional operation 1034, "REAPPLY RF SIGNAL", where the RF signal can be reactivated by the RF source (e.g., RF source 216 of FIG. 2) with the adjusted parameters via various control signals that may be provided from the controller device (e.g., controller 216). As discussed previously, the processors and controllers performing these operations are example illustrations and should not be construed as limitations on embodiments. The operations may also be performed by other computing devices or modules integrated into a single computing device or implemented as separate machines.

The operations discussed above are for illustration purposes. Integrated fiber optic spectroscopy and RF induced hyperthermia treatment may be implemented by similar processes with fewer or additional operations. In some examples, the operations may be performed in a different order. In some other examples, various operations may be eliminated. In still other examples, various operations may be divided into additional operations, or combined together into fewer operations.

Figure 11:
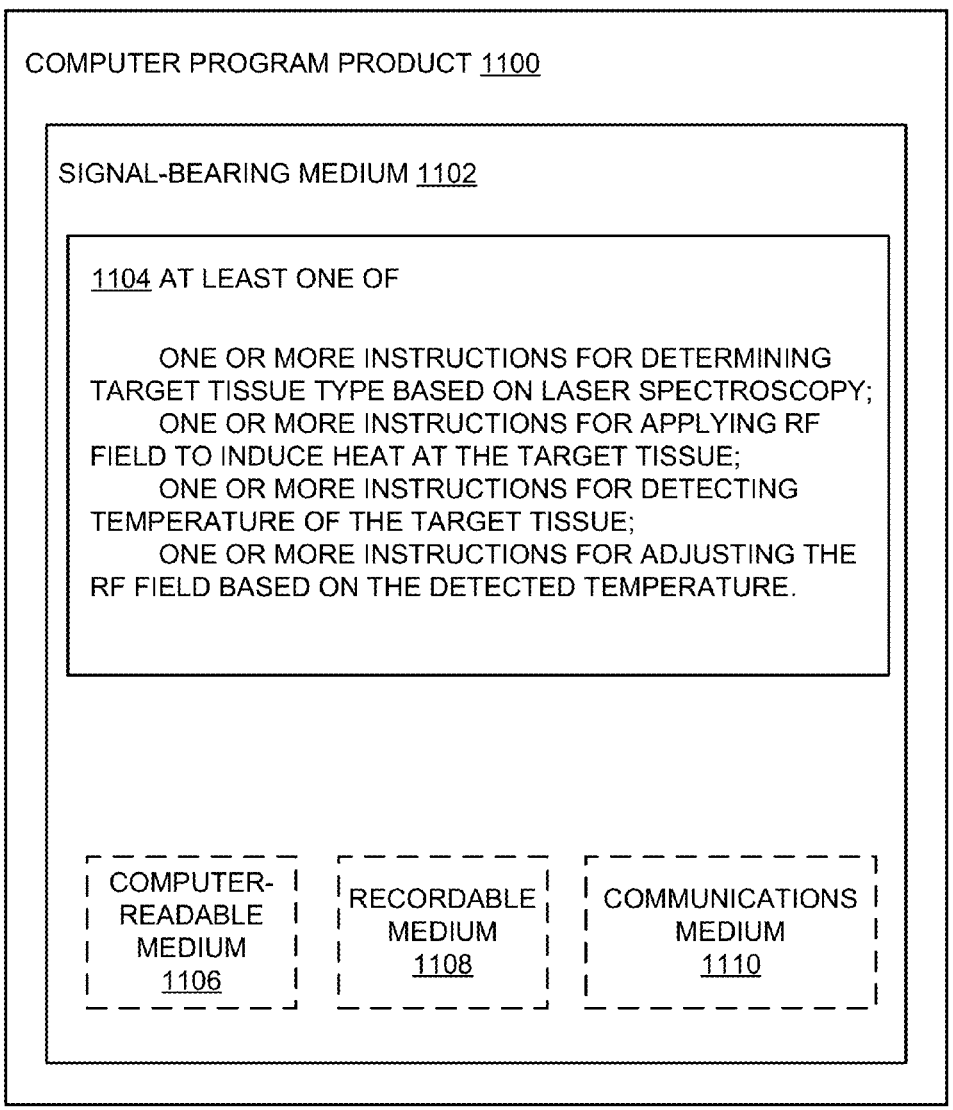
FIG. 11 illustrates a block diagram of an example computer program product, all arranged in accordance with at least some embodiments described herein.
Figure 7:
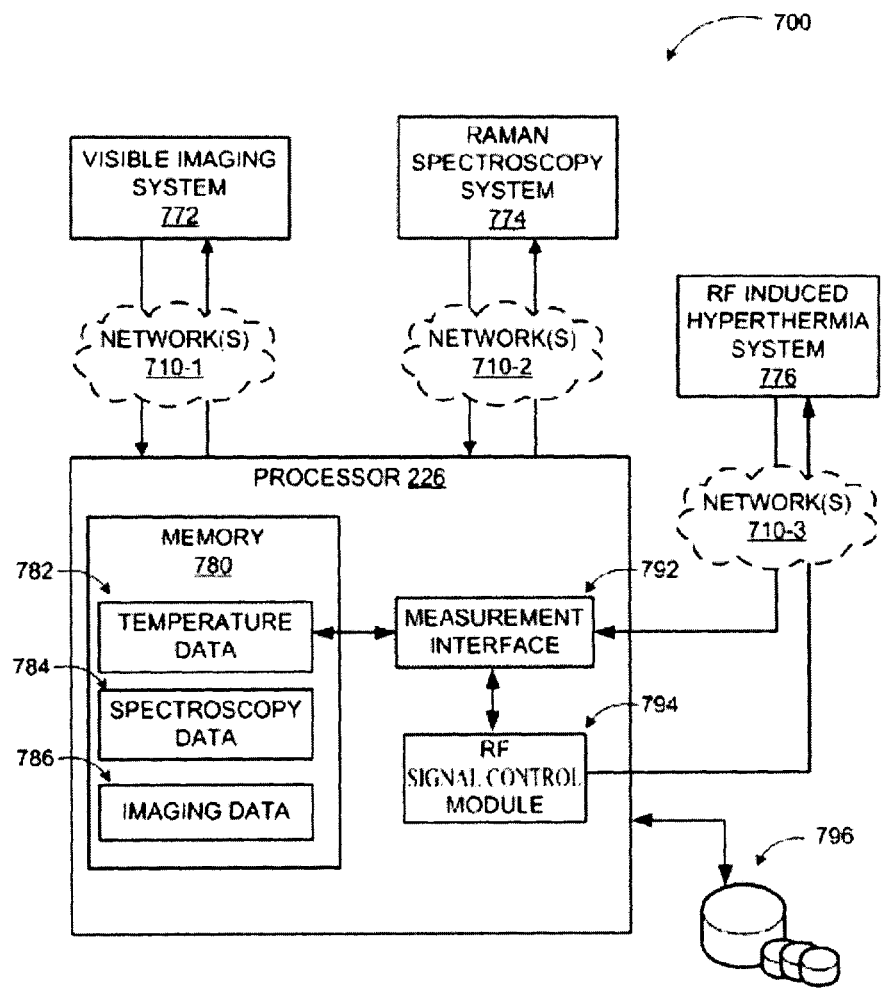
Figure 8:
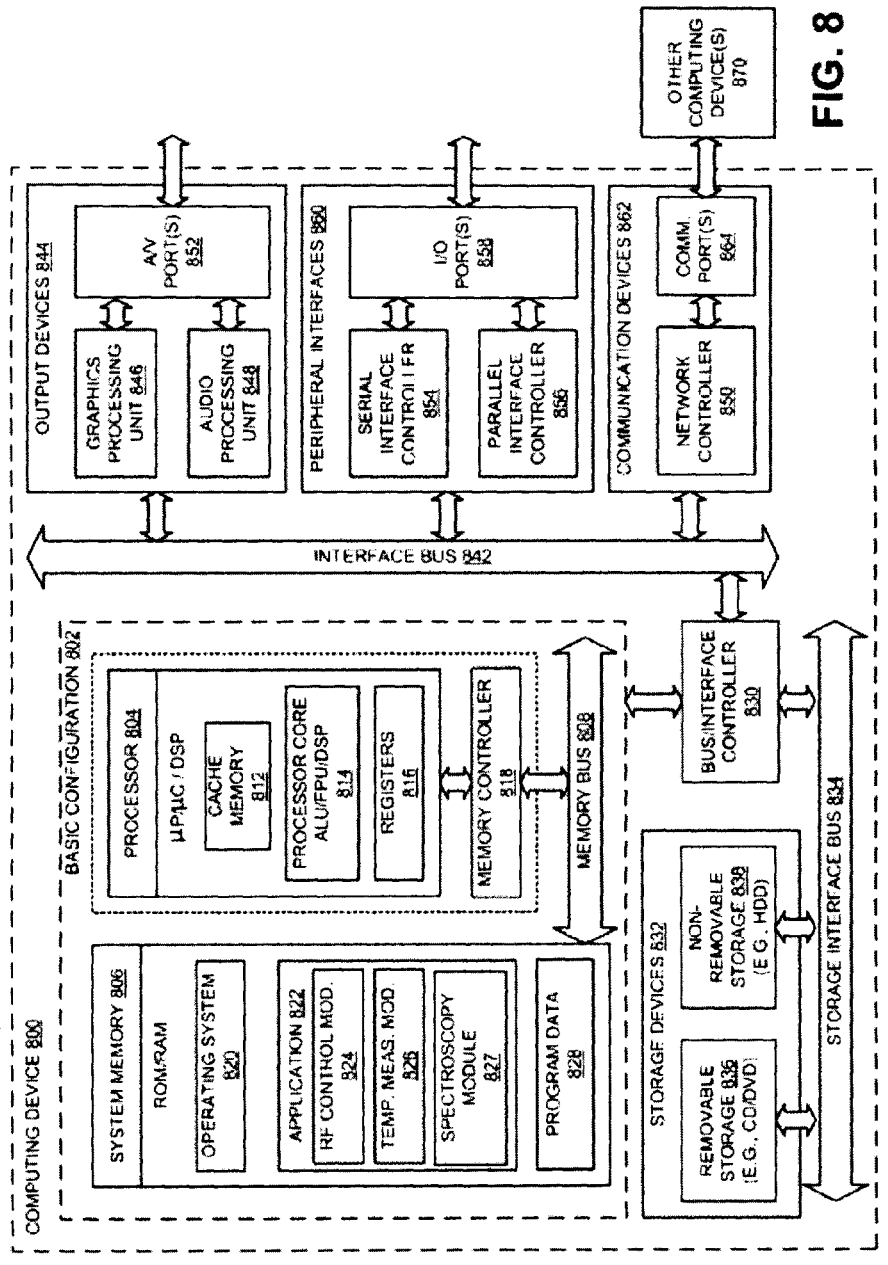
Figure 10:
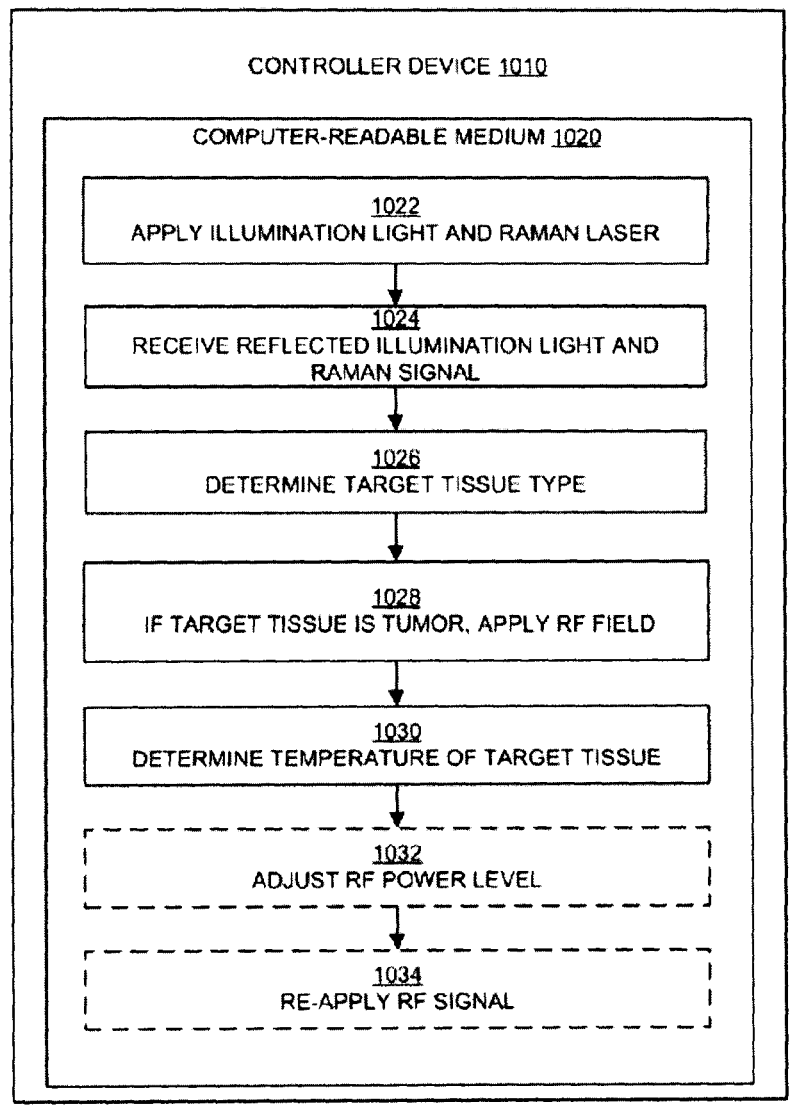

FIG. 11 illustrates a block diagram of an example computer program product 1100 arranged in accordance with at least some embodiments described herein. In some examples, as shown in FIG. 11, computer program product 1100 may include a signal bearing medium 1102 that may also include machine readable instructions 1104 that, when executed by, for example, a processor, may provide the functionality described above with respect to FIG. 2, FIG. 3, and FIG. 4. Thus, for example, referring to diagnostic/therapy device 206, one or more of the modules 212, 214, 216, and/or 218 may undertake one or more of the tasks shown in FIG. 11 in response to instructions 1104 conveyed to the diagnostic/therapy device 206 by medium 1102 to perform actions associated with controlling fiber optic spectroscopy and RF ablation as described herein. Some of those instructions may include determining target tissue type based on laser spectroscopy; applying RF field to induce heat at target tissue; detecting temperature of the target tissue; and adjusting the RF field based on detected temperature.

In some implementations, signal bearing medium 1102 depicted in FIG. 11 may encompass a computer-readable medium 1106, such as, but not limited to, a hard disk drive, a Compact Disc (CD), a Digital Video Disk (DVD), a digital tape, memory, etc. In some implementations, signal bearing medium 1102 may encompass a recordable medium 1108, such as, but not limited to, memory, read/write (R/W) CDs, R/W DVDs, etc. In some implementations, signal bearing medium 1102 may encompass a communications medium 1110, such as, but not limited to, a digital and/or an analog communication medium (e.g., a fiber optic cable, a waveguide, a wired communications link, a wireless communication link, etc.). Thus, for example, program product 1100 may be conveyed to one or more modules of the diagnostic/therapy device 206 by an RF signal bearing medium 1102, where the signal bearing medium 1102 is conveyed by a wireless communications medium 1110 (e.g., a wireless communications medium conforming with the IEEE 802.11 standard).

In accordance with some embodiments, a method for applying Radio Frequency (RF) induced hyperthermia in conjunction with fiber optic spectroscopy may be provided. The method may include detecting a target tissue by fiber optic spectroscopy through an endoscopic probe and applying an alternating electromagnetic field from an RF source through the same endoscopic probe. Detecting the target tissue may include visual detection through a visual imaging module (e.g. by illuminating an expected area within the body with visible light and detecting reflect light at a visible light detection module such as those discussed previously). The electromagnetic field may be applied by transmitting an RF signal from an RF source through the endoscopic probe. Conductive parts of the endoscopic probe may act as a waveguide or a coaxial cable enabling transmission of the RF signal as an electromagnetic wave through the probe and then radiated out to the target tissue. At the target tissue, water content may convert the RF energy into induced heat. A temperature increase at the target tissue may be controlled by a level or other parameters of the electromagnetic wave. The alternating electromagnetic field is effective to induce heat in the target tissue.

The method may further include determining an approximate temperature of the target tissue by heat sensing through the endoscopic probe and adjusting one or more of a level and/or a duration of the alternating electromagnetic field in response to the determined temperature. The temperature may be determined externally or internally using the endoscopic probe (e.g. infrared temperature sensing).

The approximate temperature may be determined through infrared (IR) sensing through at least one of the fibers in the endoscopic probe. The alternating electromagnetic field may be generated by applying an RF signal to a conductive outer shield and a conductive inner shield of the endoscopic probe, where the outer and inner shields are constructed concentrically. The target tissue may be a tumor and detecting the tumor by fiber optic spectroscopy may include detecting the target tissue by visual imaging, determining a composition of the target tissue by Raman spectroscopy, and determining whether the target tissue is a tumor based on the composition. For example, tumors may include a higher concentration of blood vessels or particular molecules compared to the surrounding tissue. Raman spectroscopy may determine a distribution of molecules and their concentration within the target tissue, which may be compared to known compositions or to that of the surrounding tissue.

Detecting the tumor by fiber optic spectroscopy may include providing a light in visible spectrum through a portion of fibers in the endoscopic probe, detecting reflected light from the target tissue for visual imaging, providing a laser signal through a central fiber in the endoscopic probe, and detecting a backscattered Raman signal from the target tissue. The Raman signal provided through the endoscopic probe may be in a spectrum between approximately 400 nm and approximately 1600 nm and the alternating electromagnetic field has a frequency between approximately 500 kHz and approximately 2.5 GHz.

In accordance with other embodiments, an apparatus for applying RF induced hyperthermia in conjunction with fiber optic spectroscopy may be provided. Such an apparatus may include a spectroscopy module adapted to provide an optical signal for Raman spectroscopy of a target tissue, an RF module adapted to provide an RF signal configured to induce temperature increase in the target tissue, and an apparatus configured to guide the optical signal and the RF signal to the target tissue.

The apparatus may also include a visual imaging module adapted to provide illumination light for the target tissue. The spectroscopy module, the RF module, and the visual imaging module may be combined in an endoscopic probe. The apparatus may further include a controller adapted to adjust one or more of an intensity of the illumination light, an intensity of the optical signal, and/or a duration and a power level of the RF signal. The controller may adjust the duration and the power level of the RF signal based on a sensed temperature of the target tissue. The controller may be an integrated module of the apparatus or a remote controller communicatively coupled to the apparatus. The remote controller may include a standalone computer, a networked computer system, a micro-processor, a micro-controller, a digital signal processor, or a special purpose processing unit. The controller may also record temperature and applied electromagnetic field information. The apparatus may also include a temperature sensing module coupled to the endoscopic probe adapted to sense a temperature of the target tissue employing infrared temperature sensing.

In accordance with further embodiments, an endoscopic probe for applying RF induced hyperthermia in conjunction with fiber optic spectroscopy may be provided. The endoscopic probe may include a center fiber adapted to carry a laser signal for Raman spectroscopy to a target tissue; a first group of fibers surrounding the center fiber adapted to carry backscattered Raman signal to a spectroscopy module; a second group of fibers surrounding the first group of fibers adapted to carry captured visible light to a microscope; a conductive inner shield surrounding the second group of fibers; a third group of fibers surrounding the conductive inner shield adapted to carry visible light to the target tissue; a fourth group of fibers dispersed among the third group of fibers adapted to guide infrared emissions to a temperature sensing module; and a conductive outer shield surrounding the third group of fibers, where the conductive inner and outer shields are configured to deliver an alternating electromagnetic field to the target tissue for inducing heat by transmitting an RF signal through the outer and inner conductive shields of the endoscopic probe.

The conductive inner and outer shields may be coupled to an RF source adapted to adjust one or more of a duration and/or power level of the RF signal based on sensed temperature of the target tissue. The outer diameter of the endoscopic probe ranges between about 1 mm and about 10 mm. The diameter of the approximately circularly assembled second group of fibers may range between about 0.5 mm and about 2 mm. The center fiber may to carry a monochromatic laser signal with a wavelength ranging between about 400 nm and about 1600 nm. The endoscopic probe may be constructed as one of a coaxial cable or a waveguide.

In accordance with yet other embodiments, a computer-readable storage medium is provided having instructions stored thereon for applying RF induced hyperthermia in conjunction with fiber optic spectroscopy. The instructions may include detecting a target tissue by visual imaging; determining a composition of the target tissue by Raman spectroscopy; determining whether the target tissue is a tumor based on the composition; if the target tissue is a tumor, applying an alternating electromagnetic field from an RF source through an endoscopic probe by transmitting an RF signal through concentrically constructed outer and inner conductive shields of the endoscopic probe, where the alternating electromagnetic field is effective to induce heat in the tumor; determining an approximate temperature of the tumor by heat sensing through the endoscopic probe; and adjusting one or more of a level and/or a duration of the RF signal in response to the determined temperature.

Detecting the target tissue by visual imaging may include providing a visible light through one or more fibers of the endoscopic probe to the target tissue, and capturing reflected visible light from the target tissue through a microscope. The instructions may further include determining the approximate temperature through a plurality of infrared (IR) sensors coupled to the fibers of the endoscopic probe and applying the RF induced hyperthermia in conjunction with one or more of surgical treatment, chemotherapy, and/or radiotherapy.

There is little distinction left between hardware and software implementations of aspects of systems; the use of hardware or software is generally (but not always, in that in certain contexts the choice between hardware and software may become significant) a design choice representing cost vs. efficiency tradeoffs. There are various vehicles by which processes and/or systems and/or other technologies described herein may be effected (e.g., hardware, software, and/or firmware), and that the preferred vehicle will vary with the context in which the processes and/or systems and/or other technologies are deployed. For example, if an implementer determines that speed and accuracy are paramount, the implementer may opt for a mainly hardware and/or firmware vehicle; if flexibility is paramount, the implementer may opt for a mainly software implementation; or, yet again alternatively, the implementer may opt for some combination of hardware, software, and/or firmware.

The foregoing detailed description has set forth various embodiments of the devices and/or processes via the use of block diagrams, flowcharts, and/or examples. Insofar as such block diagrams, flowcharts, and/or examples contain one or more functions and/or operations, it will be understood by those within the art that each function and/or operation within such block diagrams, flowcharts, or examples may be implemented, individually and/or collectively, by a wide range of hardware, software, firmware, or virtually any combination thereof. In one embodiment, several portions of the subject matter described herein may be implemented via Application Specific Integrated Circuits (ASICs), Field Programmable Gate Arrays (FPGAs), digital signal processors (DSPs), or other integrated formats. However, those skilled in the art will recognize that some aspects of the embodiments disclosed herein, in whole or in part, may be equivalently implemented in integrated circuits, as one or more computer programs running on one or more computers (e.g., as one or more programs running on one or more computer systems), as one or more programs running on one or more processors (e.g. as one or more programs running on one or more microprocessors), as firmware, or as virtually any combination thereof, and that designing the circuitry and/or writing the code for the software and or firmware would be well within the skill of one of skill in the art in light of this disclosure.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated herein, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds compositions or biological systems, which can, of course, vary. It is also to be understood that the terminology used herein is for the purpose of describing particular embodiments only, and is not intended to be limiting.

Those skilled in the art will recognize that it is common within the art to describe devices and/or processes in the fashion set forth herein, and thereafter use engineering practices to integrate such described devices and/or processes into data processing systems. That is, at least a portion of the devices and/or processes described herein may be integrated into a data processing system via a reasonable amount of experimentation. Those having skill in the art will recognize that a typical data processing system generally includes one or more of a system unit housing, a video display device, a memory such as volatile and non-volatile memory, processors such as microprocessors and digital signal processors, computational entities such as operating systems, drivers, graphical user interfaces, and applications programs, one or more interaction devices, such as a touch pad or screen, and/or control systems including feedback loops and control motors.

A typical data processing system may be implemented utilizing any suitable commercially available components, such as those typically found in data computing/communication and/or network computing/communication systems. The herein described subject matter sometimes illustrates different components contained within, or connected with, different other components. It is to be understood that such depicted architectures are merely exemplary, and that in fact many other architectures may be implemented which achieve the same functionality. In a conceptual sense, any arrangement of components to achieve the same functionality is effectively "associated" such that the desired functionality is achieved. Hence, any two components herein combined to achieve a particular functionality may be seen as "associated with" each other such that the desired functionality is achieved, irrespective of architectures or intermediate components. Likewise, any two components so associated may also be viewed as being "operably connected", or "operably coupled", to each other to achieve the desired functionality, and any two components capable of being so associated may also be viewed as being "operably couplable", to each other to achieve the desired functionality. Specific examples of operably couplable include but are not limited to physically connectable and/or physically interacting components and/or wirelessly interactable and/or wirelessly interacting components and/or logically interacting and/or logically interactable components.

With respect to the use of substantially any plural and/or singular terms herein, those having skill in the art can translate from the plural to the singular and/or from the singular to the plural as is appropriate to the context and/or application. The various singular/plural permutations may be expressly set forth herein for sake of clarity.

It will be understood by those within the art that, in general, terms used herein, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an"

should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations).

Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). In those instances where a convention analogous to "at least one of A, B, or C, etc." is used, in general such a construction is intended in the sense one having skill in the art would understand the convention (e.g., "a system having at least one of A, B, or C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

In addition, where features or aspects of the disclosure are described in terms of Markush groups, those skilled in the art will recognize that the disclosure is also thereby described in terms of any individual member or subgroup of members of the Markush group.

As will be understood by one skilled in the art, for any and all purposes, such as in terms of providing a written description, all ranges disclosed herein also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed herein can be readily broken down into a lower third, middle third and upper third, etc. As will also be understood by one skilled in the art all language such as "up to," "at least," "greater than," "less than," and the like include the number recited and refer to ranges which can be subsequently broken down into subranges as discussed above. Finally, as will be understood by one skilled in the art, a range includes each individual member. Thus, for example, a group having 1-3 cells refers to groups having 1, 2, or 3 cells. Similarly, a group having 1-5 cells refers to groups having 1, 2, 3, 4, or 5 cells, and so forth.

While various aspects and embodiments have been disclosed herein, other aspects and embodiments will be apparent to those skilled in the art. The various aspects and embodiments disclosed herein are for purposes of illustration and are not intended to be limiting, with the true scope and spirit being indicated by the following claims.

What is claimed is:

1. A method for applying Radio Frequency (RF) induced hyperthermia in conjunction with fiber optic based Raman spectroscopy, the method comprising:
    detecting a target tissue by fiber optic based Raman spectroscopy through an endoscopic probe; and
    applying an alternating electromagnetic field effective to induce heat in the target tissue from an RF source to a conductive outer shield and a conductive inner shield of the endoscopic probe, wherein the conductive outer shield and the conductive inner shield are constructed concentrically as a coaxial waveguide, and within the conductive outer shield there are one or more fibers for carrying light in visible spectrum and a laser signal.

2. The method according to claim 1, further comprising:
    determining an approximate temperature of the target tissue by heat sensing through the endoscopic probe.

3. The method according to claim 2, further comprising:
    adjusting one or more of a level and/or a duration of the alternating electromagnetic field in response to the determined temperature.

4. The method according to claim 2, further comprising:
    determining the approximate temperature through infrared (IR) sensing through at least one of the fibers in the endoscopic probe.

5. The method according to claim 1, wherein applying the alternating electromagnetic field comprises:
    applying an RF signal to the conductive outer shield and the conductive inner shield of the endoscopic probe.

6. The method according to claim 1, wherein the target tissue is a tumor and detecting the tumor by fiber optic based Raman spectroscopy comprises:
    detecting the target tissue by visual imaging;
    determining a composition of the target tissue by Raman spectroscopy; and
    determining whether the target tissue is a tumor based on the composition.

7. The method according to claim 6, wherein detecting the tumor by fiber optic based Raman spectroscopy further comprises:
    providing a light in visible spectrum through a portion of fibers in the endoscopic probe positioned between the conductive outer shield and the conductive inner shield;
    detecting reflected light from the target tissue for visual imaging;
    providing a laser signal through a central fiber in the endoscopic probe positioned within the conductive inner shield; and
    detecting backscattered Raman signal from the target tissue.

8. The method according to claim 7, wherein the Raman signal is in a spectrum between approximately 400 nm and approximately 1600 nm and the alternating electromagnetic field has a frequency between approximately 500 kHz and approximately 2.5 GHz.

9. An apparatus for applying Radio Frequency (RF) induced hyperthermia in conjunction with fiber optic based Raman spectroscopy, the apparatus comprising:
    a spectroscopy module adapted to provide an optical signal for Raman spectroscopy of a target tissue;
    an RF module adapted to provide an RF signal configured to induce heat in the target tissue; and
    an endoscopic probe configured to carry the optical signal to the target tissue, the endoscopic probe comprising a conductive outer shield and a conductive inner shield adapted to apply an alternating electromagnetic field to the target tissue responsive to the RF signal, one or more fibers positioned between the conductive outer shield and the conductive inner shield for carrying light in visible spectrum, and a fiber positioned within the conductive inner shield for carrying a laser signal.

10. The apparatus according to claim 9, further comprising:
   a visual imaging module adapted to provide illumination light for the target tissue.

11. The apparatus according to claim 10, wherein the spectroscopy module, the RF module, and the visual imaging module are combined in the endoscopic probe.

12. The apparatus according to claim 10, further comprising:
   a controller adapted to adjust one or more of an intensity of the illumination light, an intensity of the optical signal, and/or a duration and a level of the RF signal.

13. The apparatus according to claim 12, wherein the controller is further adapted to adjust the duration and the level of the RF signal based on a sensed temperature of the target tissue.

14. The apparatus according to claim 12, wherein the controller is one of an integrated module of the apparatus and a remote controller communicatively coupled to the apparatus.

15. The apparatus according to claim 14, wherein the remote controller is one of a standalone computer, a networked computer system, a micro-processor, a micro-controller, a digital signal processor, or a special purpose processing unit.

16. The apparatus according to claim 12, wherein the controller is further adapted to record temperature and applied electromagnetic field information.

17. The apparatus according to claim 9, further comprising:
   a temperature sensing module coupled to the endoscopic probe adapted to sense a temperature of the target tissue employing infrared temperature sensing.

18. An endoscopic probe for applying Radio Frequency (RF) induced hyperthermia in conjunction with fiber optic based Raman spectroscopy, comprising:
   a center fiber adapted to carry a laser signal for Raman spectroscopy to a target tissue;
   a first group of fibers surrounding the center fiber adapted to carry backscattered laser signal to a spectroscopy module;
   a second group of fibers surrounding the first group of fibers adapted to carry captured visible light to a microscope;
   a conductive inner shield surrounding the second group of fibers;
   a third group of fibers surrounding the conductive inner shield adapted to carry visible light to the target tissue;
   a fourth group of fibers dispersed among the third group of fibers adapted to provide an infrared temperature sensing signal to a temperature sensing module; and
   a conductive outer shield surrounding the third group of fibers, wherein the conductive inner and outer shields are configured to deliver an alternating electromagnetic field to the target tissue for inducing heat by transmitting an RF signal through the outer and inner conductive shields of the endoscopic probe.

19. The endoscopic probe according to claim 18, wherein the conductive inner and outer shields, are coupled to an RF source adapted to adjust one or more of a duration and/or level of the RF signal based on sensed temperature of the target tissue.

20. The endoscopic probe according to claim 18, wherein an outer diameter of the endoscopic probe ranges between about 1 mm and about 10 mm.

21. The endoscopic probe according to claim 18, wherein a diameter of the approximately circularly assembled second group of fibers ranges between about 0.5 mm and about 2 mm.

22. The endoscopic probe according to claim 18, wherein the center fiber is adapted to carry a monochromatic laser signal with a wavelength ranging between about 400 nm and about 1600 nm.

23. The endoscopic probe according to claim 18, wherein the endoscopic probe is constructed as one of a coaxial cable or a waveguide.

24. A computer-readable storage medium having instructions stored thereon for applying Radio Frequency (RF) induced hyperthermia in conjunction with fiber optic based Raman spectroscopy, the instructions comprising:
   providing a visible light through one or more fibers of an endoscopic probe to a target tissue;
   detecting the target tissue by visual imaging;
   determining a composition of the target tissue by Raman spectroscopy;
   determining whether the target tissue is a tumor based on the composition;
   if the target tissue is a tumor, applying an alternating electromagnetic field from an RF source through the endoscopic probe by transmitting an RF signal through concentrically constructed outer and inner conductive shields, of the endoscopic probe, wherein the alternating electromagnetic field is effective to induce heat in the tumor, and wherein at least a portion of the one or more fibers of the endoscopic probe are between the outer and inner conductive shields;
   determining an approximate temperature of the tumor by heat sensing through the endoscopic probe; and
   adjusting one or more of a level and/or a duration of the RF signal in response to the determined temperature.

25. The computer-readable storage medium according to claim 24, wherein detecting a target tissue by visual imaging comprises:
   capturing reflected visible light from the target tissue through a microscope.

26. The computer-readable storage medium according to claim 24, wherein the instructions further comprise:
   determining the approximate temperature through a plurality of infrared (IR) sensors coupled to the fibers of the endoscopic probe.

27. The computer-readable storage medium according to claim 24, wherein the instructions further comprise:
   applying the RF induced hyperthermia in conjunction with one or more of surgical treatment, chemotherapy, and/or radiotherapy.

* * * * *

UNITED STATES PATENT AND TRADEMARK OFFICE
CERTIFICATE OF CORRECTION

PATENT NO. : 8,874,230 B2
APPLICATION NO. : 13/121346
DATED : October 28, 2014
INVENTOR(S) : Niver et al.

It is certified that error appears in the above-identified patent and that said Letters Patent is hereby corrected as shown below:

On the Title Page, in Item (56), under "OTHER PUBLICATIONS", in Column 2, Line 1, delete "et al," and insert -- et al., --, therefor.

On Title Page 2, in Item (56), under "OTHER PUBLICATIONS", in Column 2, Line 34, delete "Laparoscopic Radi" and insert -- Laparoscopic Radio --, therefor.

On Title Page 2, in Item (56), under "OTHER PUBLICATIONS", in Column 2, Line 36, delete "Assesment" and insert -- Assessment --, therefor.

In The Drawings

In Fig. 7, Sheet 7 of 11, for Tag "794", in Line 2, delete "ADJUSTMENT" and insert -- SIGNAL CONTROL --, therefor. (See Attached)

In Fig. 8, Sheet 8 of 11, delete "UP/UC/DSP" and insert -- μP/μC/DSP --, therefor. (See Attached)

In Fig. 10, Sheet 10 of 11, in Step "1028", in Line 1, delete "TUMOR" and insert -- TUMOR, --, therefor. (See Attached)

In The Specification

In Column 10, Line 49, delete "thereof" and insert -- thereof. --, therefor.

In Column 11, Line 11, delete "thereof" and insert -- thereof. --, therefor.

In Column 11, Line 48, delete "communication device 546" and insert -- communication device 862 --, therefor.

Signed and Sealed this
Twelfth Day of May, 2015

Michelle K. Lee
*Director of the United States Patent and Trademark Office*

In Column 14, Line 9, delete "controller 216)." and insert -- controller 226). --, therefor.

In Column 17, Line 44, delete "and or" and insert -- and/or --, therefor.